United States Patent
Herpin et al.

(10) Patent No.: US 7,138,526 B1
(45) Date of Patent: Nov. 21, 2006

(54) SOLID PHASE SYNTHESIS OF N,N-DISUBSTITUTED DIAZACYCLOALKYLCARBOXY DERIVATIVES

(75) Inventors: Timothy F. Herpin, Princeton, NJ (US); George C. Morton, Collegeville, PA (US); Joseph M Salvino, Schwenksville, PA (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 650 days.

(21) Appl. No.: 10/009,621

(22) PCT Filed: Jun. 13, 2000

(86) PCT No.: PCT/US00/16243

§ 371 (c)(1), (2), (4) Date: May 14, 2002

(87) PCT Pub. No.: WO00/77519

PCT Pub. Date: Dec. 21, 2000

Related U.S. Application Data

(60) Provisional application No. 60/139,301, filed on Jun. 15, 1999.

(51) Int. Cl.
    C07D 233/72 (2006.01)

(52) U.S. Cl. ............ 548/317.1; 514/389; 544/388

(58) Field of Classification Search ............ None
See application file for complete search history.

(56) References Cited

U.S. PATENT DOCUMENTS

| | | | |
|---|---|---|---|
| 5,324,483 A | 6/1994 | Cody et al. | |
| 5,734,054 A | 3/1998 | Dolle, III | |
| 5,880,128 A * | 3/1999 | Doll et al. | 514/253.01 |

FOREIGN PATENT DOCUMENTS

WO 9858947 6/1998

OTHER PUBLICATIONS

Sarantakis, D.; Bicksler, J. J. "Solid Phase Synthesis of Sec-Amides and Removal from the Polymeric Support Under Mild Conditions" Tetrahedron Letters. 1997, 38(42), 7325-7328.*

Greene, T. H. and Wuts, P. G. M. Protective Groups in Organic Synthesis, 3rd edition, John Wiley & Sons, New York (Apr. 1999), pp. 503-507, 526 and 527.*

Kim et al., "Solid phase sythesis of benzamidine and buylamine-derived hydantoin libraries" Molecular Diversity 1998, 3, 129-132.*

Generation of a Piperazine-2-Carboxamide Library: A Practical Application of the Phenol-Sulfide React and Release Linker; Breitenbucher et al, Tet. Lett, Mar. 12, 1998, vol. 39, pp. 1295-1298.

Evaluation of a Structure-Based Statine Cyclic Diamino Amide Encoded Combinatorial Library Against Plasmepsin ii and Cathepsin D; Carroll et al, Bioorganic & Medicinal Chem Lett 8, (1998), pp. 3203-3206.

* cited by examiner

*Primary Examiner*—Jon Epperson
(74) *Attorney, Agent, or Firm*—Ronald G. Ort; George Wang

(57) ABSTRACT

A method for the solid phase synthesis of N,N-disubstituted diazacycloalkylcarboxy derivatives of general formula (I) and (II) is claimed. Examples include piperazine-2-carboxamide. The method is applicable to the synthesis or large combinatorial libraries

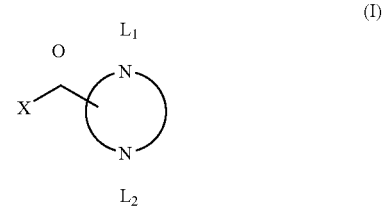

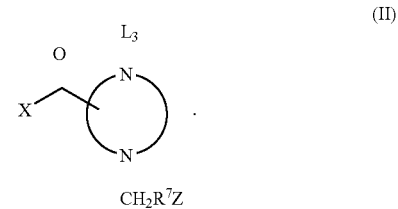

1 Claim, No Drawings

SOLID PHASE SYNTHESIS OF N,N-DISUBSTITUTED DIAZACYCLOALKYLCARBOXY DERIVATIVES

FIELD OF THE INVENTION

This invention is directed to the solid phase synthesis of N,N-disubstituted diazacycloakylcarboxy derivatives.

BACKGROUND OF THE INVENTION

Solid-phase synthetic techniques, in which a reagent is immobilized on a polymeric material which is inert to the reagents and reaction conditions employed, as well as being insoluble in the media used, are important synthetic tools. A polymeric reagent has the advantage of ease of separation from low molecular weight reactants or products by filtration or selective precipitation. The polymeric reagent can also be used in excess to effect fast and quantitative reactions such as in the case of acylations, or a large excess of reactants may be used to drive the equilibrium of the reaction towards product formation to provide essentially quantitative conversion to product, as seen in solid phase peptide synthesis. A further advantage of supported reagents and catalysts is the fact that they are recyclable and that they lend easily to automated processes. In addition, supported analogs of toxic and odorous reagents are safer to use.

Diazacycloalkyl-2-carboxy derivatives, especially piperazine-2-carboxamide groups, are present in numerous pharmacologically active compounds including, for example, farnesyl protein transferase inhibitors (See International Application No. PCT/US96/04172); platelet aggregation inhibitors (See U.S. Pat. No. 4,923,870); Factor Xa inhibitors (See International Application No. PCT/GB97/000270); alpha 1 adrenorecptor antagonists (See International Application No. PCT/US96/15223); tachykinin receptor antagonists (See U.S. Pat. No. 5,344,830); and angiotensin II antagonists (See International Application Nos. PCT/US92/04189 and PCT/US94/05789). Thus, the development of new synthetic methodology for preparing piperazine-2-carboxamides, particularly solid phase synthetic techniques which are especially useful for synthesis of large numbers of compounds through automated parallel synthesis or combinatorial library generation, is central to the rapid discovery of new therapeutic agents containing this functionality.

The solid phase synthesis of piperazine-2-carboxamide compounds is described in Breitenbucher et al., *Tetrahedron Lett.*, 1998, 39, 1295–1298, in DiIanni Carroll et al., Bioor. Med. Chem. Lett. 1998, 8, 3203 and in U.S. Pat. No. 5,734,054.

SUMMARY OF THE INVENTION

In its principle aspect, this invention is directed to a method of preparing N,N-disubstituted diazacycloakylcarboxy derivatives of formula

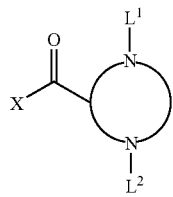

wherein

X is $NHR^1$ or OH $R^1$ is H, aliphatic or aromatic;

$L^1$ and $L^2$ are independently $-Y^1R^2$ or $-Y^2R^3$;

$R^2$ and $R^3$ are independently aliphatic or aromatic;

$Y^1$ and $Y^2$ are independently $-C(O)-$, $-C(O)O-$, $-C(O)NR^4-$ or $-SO_2-$;

$R^4$ is H, aliphatic or aromatic; and

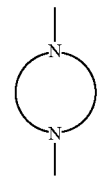

is a 5–8 membered diazaheterocyclyl ring, comprising (1) removing one of $P^1$ or $P^2$ from a resin-bound diprotected diazacycloakylcarboxy derivatives of formula

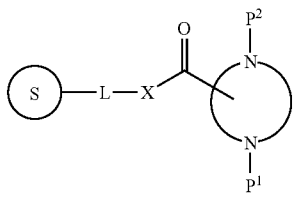

wherein

is a solid support;

L is absent or a linking group; and one of $P^1$ and $P^2$ is a base-labile nitrogen protecting group and the other of $P^1$ and $P^2$ is a Metal-labile nitrogen protecting group, (2) introducing one of $L^1$ or $L^2$, (3) removing the other of $P^1$ or $P^2$, (4) introducing the other of $L^1$ or $L^2$ and (5) isolating the diazacycloakylcarboxy derivative.

In another aspect, this invention is directed to a method of preparing a diazacycloakylcarboxy derivative of formula

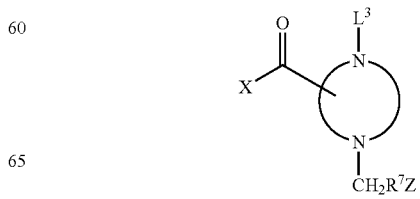

wherein

X is OH or $NR^5R^6$ $L^3$ is $-Y^3R^8$;

$Y^3$ is $-C(O)-$, $-C(O)O-$ or $-SO_2-$;

Z is $-C(O)-OR^{10}$ or $-NR^{11}R^{12}$;

$R^5$, $R^6$, $R^9$, $R^{10}$, $R^{11}$ and $R^{12}$ are independently H, aliphatic or aromatic;

$R^7$ is aliphatic or aromatic;

$R^8$ is aliphatic or aromatic; and

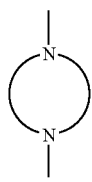

is a 5–8 membered diazaheterocyclyl ring, comprising (1) removing $P^3$ from a resin-bound diazacycloakylcarboxy derivative of formula

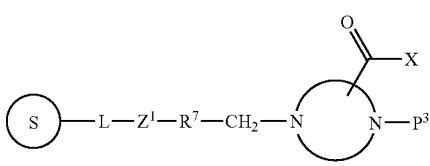

wherein

is a solid support;

L is absent or a linking group;

$P^3$ is a nitrogen protecting group;

$Z^1$ is $-OC(O)-$ or $-OC(O)-NR^{13}-$; and $R^{13}$ is H, aliphatic or aromatic, (2) introducing the group $L^3$, (3) isolating the diazacycloakylcarboxy derivative.

In another aspect, this invention is directed to a method of preparing a substituted hydantoin of formula

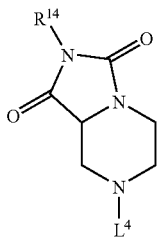

wherein $L^4$ is $Y^5R^{15}$;

$Y^5$ is $-C(O)-$, $-C(O)O-$, $-C(O)NR^{16}-$ or $-SO_2-$;

$R^{14}$ is aromatic;

$R^{15}$ is aliphatic or aromatic; and $R^{16}$ is H, aliphatic or aromatic; comprising reacting acid with a resin-bound diazacycloakylcarboxy derivative of formula

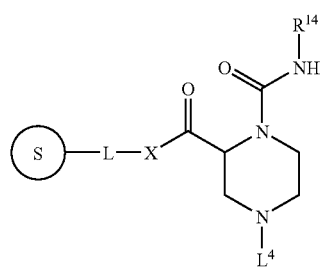

wherein

is a solid support;

X is $-O-$ or $-NR^{17}-$;

L is absent or a linking group; and $R^{17}$ is H, aliphatic or aromatic.

DETAILED DESCRIPTION OF THE INVENTION

Definitions of Terms

As used above, and throughout the description of the invention, the following terms, unless otherwise indicated, shall be understood to have the following meanings.

"Combinatorial library" or "chemical library" mean an intentionally created collection of differing molecules which can be prepared synthetically and screened for biological activity in a variety of different formats (e.g., libraries of soluble molecules; and libraries of compounds tethered to resin beads, silica chips, or other solid supports). The term is also intended to refer to an intentionally created collection of stereoisomers.

"Combinatorial synthesis" or "combinatorial chemistry" refers to an ordered strategy for the synthesis of diverse compounds by sequential addition of reagents which leads to the generation of large chemical libraries. Thus, combinatorial chemistry refers to the systematic and repetitive, covalent connection of a set of different "building blocks" of varying structures to each other to yield large arrays of diverse molecular entities.

"Diazacycloalkyl" means a non-aromatic monocyclic ring which contains 2 nitrogen atoms and from about 3 to about 6 carbon ring atoms. The diazacycloalkyl is optionally substituted with one or more "ring system substituents" which may be the same or different, and are as defined herein. Representative diazacycloakyl groups include imidazolidinyl, pyrazolidinyl, piperazinyl, homopiperazinyl, and the like.

"Diazacycloakylcarboxy derivative" means a diazacycloalkyl as defined herein in which one of the ring carbon atoms is substituted with a carboxy derivative, wherein the carboxy derivative is a carboxamide, carboxylic acid or a carboxylic ester, i.e. a group of formula —C(O)—X wherein X is OH, OR$^1$ or NR$^1$ and R$^1$ is H, aliphatic or aromatic.

"Solid support" means a substrate which is inert to the reagents and reaction conditions described herein, as well as being substantially insoluble in the media used. Representative solid supports include inorganic substrates such as kieselguhr, silica gel, and controlled pore glass; organic polymers such as polystyrene, including 1–2% copolystyrene divinyl benzene (gel form) and 20–40% copolystyrene divinyl benzene (macro porous form), polypropylene, polyethylene glycol, polyacrylamide, cellulose, and the like; and composite inorganic/polymeric compositions such as polyacrylamide supported within a matrix of kieselguhr particles. See J. M. Stewart and J. D. Young, *Solid Phase Peptide Synthesis,* 2nd. Ed., Pierce Chemical Co. (Chicago, Ill., 1984).

In addition, "solid support" includes a solid support as described above which is affixed to a second inert support such as the pins described in Technical Manual, Multipin™ SPOC, Chiron Technologies (1995) and references cited therein which comprise a detachable polyethylene- or polypropylene-based head grafted with an amino functionalized methacrylate copolymer and an inert stem.

In addition, "solid support" includes polymeric supports such as the polyethylene glycol supports described by Janda et al., *Proc. Natl. Acad. Sci. USA,* 92, 6419–6423 (1995) and S. Brenner, WO 95/16918, which are soluble in many solvents but can be precipitated by the addition of a precipitating solvent.

"Linking group" and "linker" mean a group through which a functional group such as an alcohol, a carboxylic acid, an amine or an amide may be covalently linked to the solid support. The linking group is generally inert to the reagents and reaction conditions described herein. The linking group, under chemical treatment, can release the functional group from the resin at the end of the synthesis.

"Nitrogen protecting group" means an easily removable group which is known in the art to protect an amino group against undesirable reaction during synthetic procedures and to be selectively removable. The use of N-protecting groups is well known in the art for protecting groups against undesirable reactions during a synthetic procedure and many such protecting groups are known. See for example, T. H. Greene and P. G. M. Wuts, Protective Groups in Organic Synthesis, 2nd edition, John Wiley & Sons, New York (1991), the contents of which are incorporated herein by reference. Representative nitrogen protecting groups include formyl, acetyl, chloroacetyl, trichloroacetyl, o-nitrophenylacetyl, o-nitrophenoxyacetyl, trifluoroacetyl, acetoacetyl, 4-chlorobutyryl, isobutyryl, o-nitrocinnamoyl, picolinoyl, acylisothiocyanate, aminocaproyl, benzoyl, methoxycarbonyl, 2,2,2-trifluoroethoxycarbonyl, 2-trimethylsilylethxoycarbonyl, vinyloxycarbonyl, allyloxycarbonyl, t-butyloxycarbonyl (BOC), 1,1-dimethylpropynyloxycarbonyl, benzyloxycarbonyl (CBZ), p-nitrophenylsulfinyl, p-nitrobenzyloxycarbonyl, 2,4-dichlorobenzyloxycarbonyl, allyloxycarbonyl (Alloc), 1-isopropylallyloxycarbonyl, cinnamyloxycarbonyl and 4-nitrocinnamyloxycarbonyl, 9-fluorenylmethoxycarbonyl (fmoc), 9-(2-sulfo)fluorenylmethoxycarbonyl, 9-(2,2-dibromo)fluorenylmethoxycarbonyl and the like.

"Base-labile nitrogen protecting group" means a nitrogen protecting group as defined herein which is readily removed by treatment with an amine base. Representative base-labile nitrogen protecting groups include 9-fluorenylmethoxycarbonyl (fmoc), 9-(2-sulfo)fluorenylmethoxycarbonyl, 9-(2,2-dibromo)-fluorenylmethoxycarbonyl and the like.

"Metal-labile nitrogen protecting group" means a nitrogen protecting group as defined herein which is readily removed by treatment with Pd(0). Representative Metal-labile nitrogen protecting groups include allyloxycarbonyl (Alloc), 1-isopropylallyloxycarbonyl, cinnamyloxycarbonyl, 4-nitrocinnamyloxycarbonyl, and the like.

"Symmetrical diamine" means a molecule with two identical amino groups. Examples of symmetrical diamines include piperazine, 4-amino-aniline, and 4-aminomethylbenzylamine.

"Aliphatic" means a radical derived from a non aromatic C—H bond by removal of the hydrogen atom. The aliphatic radical may be further substituted by additional aliphatic or aromatic radicals. Representative aliphatic groups include alkyl, alkenyl, alkynyl, cycloalkyl, cycloalkenyl, heterocyclyl, heterocyclenyl, aralkenyl, aralkyloxyalkyl, aralkyloxycarbonylalkyl, aralkyl, aralkynyl, aralkyloxyalkenyl, heteroaralkenyl, heteroaralkyl, heteroaralkyloxyalkenyl, heteroaralkyloxyalkyl, heteroaralkynyl, fused arylcycloalkyl, fused heteroarylcycloalkyl, fused arylcycloalkenyl, fused heteroarylcycloalkenyl, fused arylheterocyclyl, fused heteroarylheterocyclyl, fused arylheterocyclenyl, fused heteroarylheterocyclenyl as used herein. "Aliphatic", as used herein, also encompasses the residual, non-carboxyl portion of natural and unnatural amino acids as defined herein.

"Aromatic" means a radical derived from an aromatic C—H bond by removal of the hydrogen atom. Aromatic includes both aryl and heteroaryl rings as defined herein. The aryl or heteroaryl ring may be further substituted by additional aliphatic or aromatic radicals as defined herein. Representative aromatic groups include aryl, fused cycloalkenylaryl, fused cycloalkylaryl, fused heterocyclylaryl, fused heterocyclenylaryl, heteroaryl, fused cycloalkylheteroaryl, fused cycloalkenylheteroaryl, fused heterocyclenylheteroaryl, fused heterocyclylheteroaryl, and the like.

"Acyl" means an H—CO— or alkyl-CO— group wherein the alkyl group is as defined herein. Preferred acyls contain a lower alkyl. Exemplary acyl groups include formyl, acetyl, propanoyl, 2-methylpropanoyl, butanoyl and palmitoyl.

"Acylamino" is an acyl-NH— group wherein acyl is as defined herein.

"Alkenoyl" means an alkenyl-CO— group wherein alkenyl is as defined herein.

"Alkenyl" means a straight or branched aliphatic hydrocarbon group of 2 to about 15 carbon atoms which contains at least one carbon—carbon double bond. Preferred alkenyl groups have 2 to about 12 carbon atoms; more preferred alkenyl groups have 2 to about 4 carbon atoms. The alkenyl group is optionally substituted with one or more alkyl group substituents as defined herein. Representative alkenyl groups include ethenyl, propenyl, n-butenyl, i-butenyl, 3-methylbut-2-enyl, n-pentenyl, heptenyl, octenyl, cyclohexylbutenyl and decenyl.

"Alkenyloxy" means an alkenyl-O— group wherein the alkenyl group is as defined herein. Representative alkenyloxy groups include allyloxy or 3-butenyloxy.

"Alkoxy" means an alkyl-O— group wherein the alkyl group is as defined herein. Representative alkoxy groups include methoxy, ethoxy, n-propoxy, i-propoxy, n-butoxy, heptoxy, and the like.

"Alkoxyalkyl" means an alkyl-O-alkylene- group wherein alkyl and alkylene are as defined herein. Representative alkoxyalkyl groups include methoxyethyl, ethoxymethyl, n-butoxymethyl and cyclopentylmethyloxyethyl.

"Alkoxyalkoxy" means an alkyl-O-alkylenyl-O— group. Representative alkoxyalkoxy include methoxymethoxy, methoxyethoxy, ethoxyethoxy, and the like.

"Alkoxycarbonyl" means an ester group; i.e. an alkyl-O—CO— group wherein alkyl is as defined herein. Representative alkoxycarbonyl groups include methoxycarbonyl, ethoxycarbonyl, t-butyloxycarbonyl, and the like.

"Alkoxycarbonylalkyl" means an alkyl-O—CO-alkylene- group wherein alkyl and alkylene are as defined herein. Representative alkoxycarbonylalkyl include methoxycarbonylmethyl, and ethoxycarbonylmethyl, methoxycarbonyl ethyl, and the like.

"Alkyl" means an aliphatic hydrocarbon group which may be a straight chain, or branched chain, having about 1 to about 20 carbon atoms in the chain. Preferred alkyl groups have 1 to about 12 carbon atoms in the chain. Branched means that one or more lower alkyl groups such as methyl, ethyl or propyl are attached to a linear alkyl chain. "Lower alkyl" means about 1 to about 4 carbon atoms in the chain which may be straight or branched. The alkyl is optionally substituted with one or more "alkyl group substituents" which may be the same or different, and include halo, cycloalkyl, hydroxy, alkoxy, amino, carbamoyl, acylamino, aroylamino, carboxy, alkoxycarbonyl, aralkyloxycarbonyl, and heteroaralkyloxycarbonyl. Representative alkyl groups include methyl, trifluoromethyl, cyclopropylmethyl, cyclopentylmethyl, ethyl, n-propyl, i-propyl, n-butyl, 1-butyl, n-pentyl, 3-pentyl, methoxyethyl, carboxymethyl, methoxycarbonylethyl, benzyloxycarbonylmethyl, and pyridylmethyloxycarbonylmethyl.

"Alkylene" means a straight or branched bivalent hydrocarbon chain of 1 to about 6 carbon atoms. The alkylene is optionally substituted with one or more "alkylene group substituents" which may be the same or different, and include halo, cycloalkyl, hydroxy, alkoxy, carbamoyl, carboxy, cyano, aryl, heteroaryl or oxo. The alkylene is optionally interrupted by, i.e., a carbon within the alkylene moiety is substituted for, —O—, —S(O)$_m$ (where m is 0–2), phenylene or —NR'—(where R' is lower alkyl). Preferred alkylene groups are the lower alkylene groups having 1 to about 4 carbon atoms. Representative alkylene groups include methylene, ethylene, and the like.

"Alkenylene" means a straight or branched bivalent hydrocarbon chain containing at least one carbon—carbon double bond. The alkenylene is optionally substituted with one or more "alkylene group substituents" as defined herein. The alkenylene is optionally interrupted by, i.e., a carbon within the alkenylene moiety is substituted for, —O—, —S(O)$_m$ (where m is 0–2), phenylene or —NR'— (where R' is lower alkyl). Representative alkenylene groups include —CH═CH—, —CH$_2$CH═CH—, —C(CH$_3$)═CH—, —CH$_2$CH═CHCH$_2$—, and the like.

"Alkynylene" means a straight or branched bivalent hydrocarbon chain containing at least one carbon—carbon triple bond. The alkynylene is optionally substituted with one or more "alkylene group substituents" as defined herein. The alkynylene is optionally interrupted by, i.e., a carbon thereof is substituted for, —O—, —S(O)$_m$ (where m is 0–2), phenylene or —NR'— (where R' is lower alkyl). Representative alkynylene include —CH≡CH—, —CH≡CH—CH$_2$—, —CH≡CH—CH(CH$_3$)—, and the like.

"Alkylsulfinyl" means an alkyl-SO— group wherein the alkyl group is as defined herein. Preferred alkylsulfinyl groups are those wherein the alkyl group is lower alkyl.

"Alkylsulfonyl" means an alkyl-SO$_2$-group wherein the alkyl group is as defined herein. Preferred alkylsulfonyl groups are those wherein the alkyl group is lower alkyl.

"Alkylsulfonylcarbamoyl" means an alkyl-SO$_2$—NH—CO— group wherein the alkyl group is as defined herein. Preferred alkylsulfonylcarbamoyl groups are those wherein the alkyl group is lower alkyl.

"Alkylthio" means an alkyl-S— group wherein the alkyl group is as defined herein. Preferred alkylthio groups are those wherein the alkyl group is lower alkyl. Representative alkylthio groups include methylthio, ethylthio, i-propylthio, heptylthio, and the like.

"Alkynyl" means a straight chain, or branched chain, aliphatic hydrocarbon group of 2 to about 15 carbon atoms which contains at least one carbon—carbon triple bond. Preferred alkynyl groups have 2 to about 12 carbon atoms. More preferred alkynyl groups contain 2 to about 4 carbon atoms. "Lower alkynyl" means alkynyl of 2 to about 4 carbon atoms. The alkynyl group may be substituted by one or more alkyl group substituents as defined herein. Representative alkynyl groups include ethynyl, propynyl, n-butynyl, 2-butynyl, 3-methylbutynyl, n-pentynyl, heptynyl, octynyl, decynyl, and the like.

"Alkynyloxy" means an alkynyl-O— group wherein the alkynyl group is as defined herein. Representative alkynyloxy groups include propynyloxy, 3-butynyloxy, and the like.

"Alkynyloxyalkyl" means alkynyl-O-alkylene- group wherein the alkynyl and alkylene are as defined herein.

"Amidino" or "amidine" means a group of formula

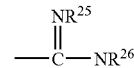

wherein R$^{25}$ is selected from hydrogen; R$^{27}$O—; R$^{27}$C(O)—; R$^{27}$O$_2$C— wherein R$^{27}$ is hydrogen, alkyl, aralkyl or heteroaralkyl; cyano; alkyl; nitro; and amino, and R$^{26}$ is selected from hydrogen; alkyl; aralkyl; and heteroaralkyl.

"Amino" means a group of formula Y$^{1b}$Y$^{2b}$N— wherein Y$^{1b}$ and Y$^{2b}$ are independently hydrogen; acyl; or alkyl, or Y$^{1b}$ and Y$^{2b}$ taken together with the N through which Y$^{1b}$ and Y$^{2b}$ are linked form a 4 to 7 membered azaheterocyclyl. Representative amino groups include amino (H$_2$N—), methylamino, dimethylamino, diethylamino, and the like.

"Aminoalkyl" means an amino-alkylene- group wherein amino and alkylene are as defined herein. Representative aminoalkyl groups include aminomethyl, aminoethyl, dimethylaminomethyl, and the like.

"Aralkenyl" means an aryl-alkenylene- group wherein the aryl and alkenylene are define herein. Preferred aralkenyl groups contain a lower alkenylene moiety. A representative aralkenyl group is 2-phenethenyl.

"Aralkyloxy" means an aralkyl-O— group wherein aralkyl group is as defined herein. Representative aralkoxy groups include benzyloxy, naphth-1-ylmethoxy, naphth-2-ylmethoxy, and the like.

"Aralkyloxyalkyl" means an aralkyl-O-alkylene- group wherein the aralkyl and the alkylene are as defined herein. A representative aralkyloxyalkyl group is benzyloxyethyl.

"Aralkyloxycarbonyl" means an aralkyl-O—CO— group wherein aralkyl is as defined herein. A representative aralkoxycarbonyl group is benzyloxycarbonyl.

"Aralkyloxycarbonylalkyl" means an aralkoxycarbonyl-alkylene- wherein aralkyloxycarbonyl and alkylene are as defined herein. Representative aralkoxycarbonylalkyls include benzyloxycarbonylmethyl, benzyloxycarbonylethyl.

"Aralkyl" means an aryl-alkylene- group wherein the aryl and alkylene are as defined herein. Preferred aralkyls contain a lower alkyl moiety. Representative aralkyl groups include benzyl, 2-phenethyl, naphthlenemethyl, and the like.

"Aralkyloxyalkenyl" means an aralkyl-O-alkenylene-group wherein the aralkyl and alkenylene are as defined herein. A representative aralkyloxyalkenyl group is 3-benzyloxyallyl.

"Aralkylsulfonyl" means an aralkyl-SO$_2$— group wherein the aralkyl is as defined herein.

"Aralkylsulfinyl" means an aralkyl-SO— group wherein the aralkyl is as defined herein.

"Aralkylthio" means an aralkyl-S— group wherein the aralkyl is as defined herein. A representative aralkylthio group is benzylthio.

"Aroyl" means an aryl-CO— group wherein the aryl is as defined herein. Representative aroyl include benzoyl, naphth-1-oyl and naphth-2-oyl.

"Cycloalkyl" means a non-aromatic mono- or multicyclic ring system of about 3 to about 10 carbon atoms, preferably of about 5 to about 10 carbon atoms. Preferred cycloalkyl rings contain about 5 to about 6 ring atoms. The cycloalkyl is optionally substituted with one or more "ring system substituents" which may be the same or different, and are as defined herein. Representative monocyclic cycloalkyl include cyclopentyl, cyclohexyl, cycloheptyl, and the like. Representative multicyclic cycloalkyl include 1-decalin, norbornyl, adamantyl, and the like. The prefix spiro before cycloalkyl means that geminal substituents on a carbon atom are replaced to form 1,1-cycloalkyl.

"Cycloalkylene" means a bivalent radical derived from a cycloalkyl as defined herein by removal of a hydrogen atom from each of two ring atoms. Preferred cycloalkylenes have about 4 to about 8 carbon atoms. Preferred cycloalkylenene groups include cis or trans 1,2-, 1,3-, or 1,4-cyclohexylene.

"Cycloalkenyl" means a non-aromatic mono- or multicyclic ring system of about 3 to about 10 carbon atoms, preferably of about 5 to about 10 carbon atoms which contains at least one carbon—carbon double bond. Preferred cycloalkylene rings contain about 5 to about 6 ring atoms. The cycloalkenyl is optionally substituted with one or more "ring system substituents" which may be the same or different, and are as defined herein. Representative monocyclic cycloalkenyl groups include cyclopentenyl, cyclohexenyl, cycloheptenyl, and the like. A representative multicyclic cycloalkenyl groups is norbornylenyl.

"Heterocyclenyl" means a non-aromatic monocyclic or multicyclic ring system of about 3 to about 10 ring atoms, preferably about 5 to about 10 ring atoms, in which one or more of the atoms in the ring system is/are element(s) other than carbon, for example a nitrogen, oxygen or sulfur atoms, and which contains at least one carbon—carbon double bond or carbon-nitrogen double bond. Preferred heterocyclenyl rings contain about 5 to about 6 ring atoms. The prefix aza, oxa or thia before heterocyclenyl means that at least a nitrogen, oxygen or sulfur atom respectively is present as a ring atom. The heterocyclenyl is optionally substituted by one or more ring system substituents, which may be the same or different, wherein "ring system substituent" is as defined herein. The nitrogen or sulphur atom of the heterocyclenyl is optionally oxidized to the corresponding N-oxide, S-oxide or S,S-dioxide. Representative monocyclic azaheterocyclenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like. Representative oxaheterocyclenyl groups include 3,4-dihydro-2H-pyran, dihydrofuranyl, fluorodihydrofuranyl, and the like. A representative multicyclic oxaheterocyclenyl group is 7-oxabicyclo[2.2.1]heptenyl. Representative monocyclic thia-heterocyclenyl groups include dihydrothiophenyl, dihydrothiopyranyl, and the like.

"Heterocyclyl" means a non-aromatic saturated monocyclic or multicyclic ring system of about 3 to about 10 ring atoms, preferably about 5 to about 10 ring atoms, in which one or more of the atoms in the ring system is/are element(s) other than carbon, for example nitrogen, oxygen or sulfur. Preferred heterocyclyls contain about 5 to 6 ring atoms. The prefix aza, oxa or thia before heterocyclyl means that at least a nitrogen, oxygen or sulfur atom respectively is present as a ring atom. The heterocyclyl is optionally substituted by one or more "ring system substituents" which may be the same or different, and are as defined herein. Representative monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Aryl" means an aromatic monocyclic or multicyclic ring system of 6 to about 14 carbon atoms, preferably of about 6 to about 10 carbon atoms. The aryl is optionally substituted with one or more "ring system substituents" which may be the same or different, and are as defined herein. Representative aryl groups include phenyl and naphthyl.

"Heteroaryl" means an aromatic monocyclic or multicyclic ring system of about 5 to about 14 ring atoms, preferably about 5 to about 10 ring atoms, in which one or more of the atoms in the ring system is/are element(s) other than carbon, for example nitrogen, oxygen or sulfur. Preferred heteroaryls contain about 5 to 6 ring atoms. The "heteroaryl" is optionally substituted by one or more "ring system substituents" which may be the same or different, and are as defined herein. The prefix aza, oxa or thia before heteroaryl means that at least a nitrogen, oxygen or sulfur atom respectively is present as a ring atom. A nitrogen atom of a heteroaryl is optionally oxidized to the corresponding N-oxide. Representative heteroaryls include pyrazinyl, furanyl, thienyl, pyridyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridine, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Fused arylcycloalkenyl" means a radical derived from a fused aryl and cycloalkenyl as defined herein by removal of hydrogen atom from the cycloalkenyl portion. Preferred fused arylcycloalkenyls are those wherein aryl is phenyl and the cycloalkenyl consists of about 5 to about 6 ring atoms. The fused arylcycloalkenyl is optionally substituted by one or more ring system substituents, which may be the same or different, wherein "ring system substituent" is as defined herein. Representative fused arylcycloalkenyl include 1,2-dihydronaphthylene, indene, and the like, in which the bond to the parent moiety is through a non-aromatic carbon atom.

"Fused cycloalkenylaryl" means a radical derived from a fused arylcycloalkenyl as defined herein by removal of hydrogen atom from the aryl portion. Representative fused cycloalkenylaryl are as described herein for a fused arylcycloalkenyl, except that the bond to the parent moiety is through an aromatic carbon atom. The fused cycloalkenylaryl is optionally substituted by one or more ring system substituents, which may be the same or different, wherein "ring system substituent" is as defined herein.

"Fused arylcycloalkyl" means a radical derived from a fused aryl and cycloalkyl as defined herein by removal of a hydrogen atom from the cycloalkyl portion. Preferred fused arylcycloalkyls are those wherein aryl is phenyl and the cycloalkyl consists of about 5 to about 6 ring atoms. The fused arylcycloalkyl is optionally substituted by one or more ring system substituents, which may be the same or different, wherein "ring system substituent" is as defined herein. Representative fused arylcycloalkyl includes 1,2,3,4-tetrahydronaphthyl, and the like, in which the bond to the parent moiety is through a non-aromatic carbon atom.

"Fused cycloalkylaryl" means a radical derived from a fused arylcycloalkyl as defined herein by removal of a hydrogen atom from the aryl portion. Representative fused cycloalkylaryl are as described herein for a fused arylcycloalkyl radical, except that the bond to the parent moiety is through an aromatic carbon atom. The fused cycloalkylaryl is optionally substituted by one or more ring system substituents, which may be the same or different, wherein "ring system substituent" is as defined herein.

"Fused arylheterocyclenyl" means a radical derived from a fused aryl and heterocyclenyl as defined herein by removal of a hydrogen atom from the heterocyclenyl portion. Preferred fused arylheterocyclenyls are those wherein aryl is phenyl and the heterocyclenyl consists of about 5 to about 6 ring atoms. The prefix aza, oxa or thia before the heterocyclenyl portion of the fused arylheterocyclenyl means that at least a nitrogen, oxygen or sulfur atom respectively is present as a ring atom. The fused arylheterocyclenyl is optionally substituted by one or more ring system substituents, which may be the same or different, wherein "ring system substituent" is as defined herein. The nitrogen or sulphur atom of the heterocyclyl portion of the fused arylheterocyclenyl is optionally oxidized to the corresponding N-oxide, S-oxide or S,S-dioxide. Representative fused arylheterocyclenyl include 3H-indolinyl, 1H-2-oxoquinolyl, 2H-1-oxoisoquinolyl, 1,2-dihydroquinolinyl, 3,4-dihydroquinolinyl, 1,2-dihydroisoquinolinyl, 3,4-dihydroisoquinolinyl, and the like, in which the bond to the parent moiety is through a non-aromatic carbon or nitrogen atom.

"Fused heterocyclenylaryl" means a radical derived from a fused arylheterocyclenyl as defined herein by removal of a hydrogen atom from the aryl portion. Representative fused heterocyclenylaryl are as defined herein for a fused arylheterocyclenyl radical, except that the bond to the parent moiety is through an aromatic carbon atom. The fused heterocyclenylaryl is optionally substituted by one or more ring system substituents, which may be the same or different, wherein "ring system substituent" is as defined herein.

"Fused arylheterocyclyl" means a radical derived from a fused aryl and heterocyclyl as defined herein by removal of a hydrogen atom from the heterocyclyl portion. Preferred fused arylheterocyclyls are those wherein aryl is phenyl and the heterocyclyl consists of about 5 to about 6 ring atoms. The prefix aza, oxa or thia before heterocyclyl means that at least a nitrogen, oxygen or sulfur atom respectively is present as a ring atom. The fused arylheterocyclyl is optionally substituted by one or more ring system substituents, which may be the same or different, wherein "ring system substituent" is as defined herein. The fused arylheterocyclyl is optionally substituted by one or more ring system substituents, which may be the same or different, wherein "ring system substituent" is as defined herein. The nitrogen or sulphur atom of the heterocyclyl portion of the fused arylheterocyclyl is optionally oxidized to the corresponding N-oxide, S-oxide or S,S-dioxide. Representative preferred fused arylheterocyclyl ring systems include phthalimide, 1,4-benzodioxane, indolinyl, 1,2,3,4-tetrahydroisoquinoline, 1,2,3,4-tetrahydroquinoline, 1H-2,3-dihydroisoindolyl, 2,3-dihydrobenz[f]isoindolyl, 1,2,3,4-tetrahydrobenz[g]isoquinolinyl, and the like, in which the bond to the parent moiety is through a non-aromatic carbon atom.

"Fused heterocyclylaryl" means a radical derived from a fused aryheterocyclyl as defined herein by removal of a hydrogen atom from the heterocyclyl portion. The fused heterocyclylaryl is optionally substituted by one or more ring system substituents, which may be the same or different, wherein "ring system substituent" is as defined herein. Representative preferred fused heterocyclylaryl ring systems are as described for fused arylheterocyclyl, except that the bond to the parent moiety is through an aromatic carbon atom.

"Fused heteroarylcycloalkenyl" means a radical derived from a fused heteroaryl and cycloalkenyl as defined herein by removal of a hydrogen atom from the cycloalkenyl portion. Preferred fused heteroarylcycloalkenyls are those wherein the heteroaryl and the cycloalkenyl each contain about 5 to about 6 ring atoms. The prefix aza, oxa or thia before heteroaryl means that at least a nitrogen, oxygen or sulfur atom respectively is present as a ring atom. The fused heteroarylcycloalkenyl is optionally substituted by one or more ring system substituents, wherein "ring system substituent" is as defined herein. The nitrogen atom of the heteroaryl portion of the fused heteroarylcycloalkenyl is optionally oxidized to the corresponding N-oxide. Representative fused heteroarylcycloalkenyl include 5,6-dihydroquinolyl, 5,6-dihydroisoquinolyl, 5,6-dihydroquinoxalinyl, 5,6-dihydroquinazolinyl, 4,5-dihydro-1H-benzimidazolyl, 4,5-dihydrobenzoxazolyl, and the like, in which the bond to the parent moiety is through a non-aromatic carbon atom.

"Fused cycloalkenylheteroaryl" means a radical derived from a fused heteroarylcycloalkenyl as defined herein by removal of a hydrogen atom from the heteroaryl portion. The fused cycloalkenylheteroaryl is optionally substituted by one or more ring system substituents, wherein "ring system substituent" is as defined herein. Representative fused cycloalkenylheteroaryl are as described herein for fused heteroarylcycloalkenyl, except that the bond to the parent moiety is through an aromatic carbon atom.

"Fused heteroarylcycloalkyl" means a radical derived from a fused heteroaryl and cycloalkyl as defined herein by removal of a hydrogen atom from the cycloalkyl portion. Preferred fused heteroarylcycloalkyls are those wherein the heteroaryl thereof consists of about 5 to about 6 ring atoms and the cycloalkyl consists of about 5 to about 6 ring atoms. The prefix aza, oxa or thia before heteroaryl means that at least a nitrogen, oxygen or sulfur atom is present respectively as a ring atom. The fused heteroarylcycloalkyl is optionally substituted by one or more ring system substituents, wherein "ring system substituent" is as defined herein. The nitrogen atom of the heteroaryl portion of the fused heteroarylcycloalkyl is optionally oxidized to the corresponding N-oxide. Representative fused heteroarylcycloalkyl include 5,6,7,8-tetrahydroquinolinyl, 5,6,7,8-tetrahydroisoquinolyl, 5,6,7,8-tetrahydroquinoxalinyl, 5,6,7,8-tetrahydroquinazolyl, 4,5,6,7-tetrahydro-1H-benzimidazolyl, 4,5,6,7-tetrahydrobenzoxazolyl, 1H-4-oxa-1,5-diazanaphthalen-2-onyl, 1,3-dihydroimidizole-[4,5]- pyridin-2-onyl, and the like, in which the bond to the parent moiety is through a non-aromatic carbon atom.

"Fused cycloalkylheteroaryl" means a radical derived from a fused heteroarylcycloalkyl as defined herein by removal of a hydrogen atom from the heteroaryl portion. The fused cycloalkylheteroaryl is optionally substituted by one or more ring system substituents, wherein "ring system substituent" is as defined herein. Representative fused cycloalkylheteroaryl are as described herein for fused heteroarylcycloalkyl, except that the bond to the parent moiety is through an aromatic carbon atom.

"Fused heteroarylheterocyclenyl" means a radical derived from a fused heteroaryl and heterocyclenyl as defined herein by the removal of a hydrogen atom from the heterocyclenyl portion. Preferred fused heteroarylheterocyclenyls are those wherein the heteroaryl thereof consists of about 5 to about 6 ring atoms and the heterocyclenyl consists of 4 to 7, preferably, about 5 to 6 ring atoms. The prefix aza, oxa or thia before heteroaryl or heterocyclenyl means that at least a nitrogen, oxygen or sulfur atom is present respectively as a ring atom. The fused heteroarylheterocyclenyl is optionally substituted by one or more ring system substituents, which may be the same or different, wherein "ring system substituent" is as defined herein. The nitrogen atom of the heteroaryl portion of the fused heteroarylheterocyclenyl is optionally oxidized to the corresponding N-oxide. The nitrogen or sulphur atom of the heterocyclenyl portion of the fused heteroarylheterocyclenyl is optionally oxidized to the corresponding N-oxide, S-oxide or S,S-dioxide. Representative fused heteroarylheterocyclenyl include 7,8-dihydro[1,7]naphthyridinyl, 1,2-dihydro[2,7]naphthyridinyl, 6,7-dihydro-3H-imidazo[4,5-c]pyridyl, 1,2-dihydro-1,5-naphthyridinyl, 1,2-dihydro-1,6-naphthyridinyl, 1,2-dihydro-1,7-naphthyridinyl, 1,2-dihydro-1,8-naphthyridinyl, 1,2-dihydro-2,6-naphthyridinyl, and the like, in which the bond to the parent moiety is through a non aromatic carbon or nitrogen atom.

"Fused heterocyclenylheteroaryl" means a radical derived from a fused heteroarylheterocyclenyl as defined herein by the removal of a hydrogen atom from the heteroaryl portion. The fused heterocyclenylheteroaryl is optionally substituted by one or more ring system substituents, wherein "ring system substituent" is as defined herein. Representative fused heterocyclenylheteroaryl are as described herein for fused heteroarylheterocyclenyl, except that the bond to the parent moiety is through an aromatic carbon atom.

"Fused heteroarylheterocyclyl" means a radical derived from a fused heteroaryl and heterocyclyl as defined herein, by removal of a hydrogen atom from the heterocyclyl portion. Preferred fused heteroarylheterocyclyls are those wherein the heteroaryl thereof consists of 4 to 7, preferably 5 to 6 ring atoms and the heterocyclyl consists of 4 to 7, preferably 5 to 6 ring atoms. The prefix aza, oxa or thia before the heteroaryl or heterocyclyl portion of the fused heteroarylheterocyclyl means that at least a nitrogen, oxygen or sulfur atom respectively is present as a ring atom. The fused heteroarylheterocyclyl is optionally substituted by one or more ring system substituents, wherein "ring system substituent" is as defined herein. The nitrogen atom of the heteroaryl portion of the fused heteroarylheterocyclyl is optionally oxidized to the corresponding N-oxide. The nitrogen or sulphur atom of the heterocyclyl portion of the fused heteroarylheterocyclyl is optionally oxidized to the corresponding N-oxide, S-oxide or S,S-dioxide. Representative fused heteroarylheterocyclyl include 2,3-dihydro-1H pyrrol [3,4-b]quinolin-2-yl, 1,2,3,4-tetrahydrobenz [b][1,7]naphthyridin-2-yl, 1,2,3,4-tetrahydrobenz [b][1,6]naphthyridin-2-yl, 1,2,3,4-tetrahydro-9H-pyrido[3,4-b]indol-2-yl, 1,2,3,4-tetrahydro-9H-pyrido[4,3-b]indol-2-yl, 2,3,-dihydro-1H-pyrrolo[3,4-b]indol-2-yl, 1H-2,3,4,5-tetrahydroazepino[3,4-b]indol-2-yl, 1H-2,3,4,5-tetrahydroazepino[4,3-b]indol-3-yl, 1H-2,3,4,5-tetrahydroazepino[4,5-b]indol-2-yl, 5,6,7,8-tetrahydro[1,7]napthyridinyl, 1,2,3,4-tetrhydro[2,7]naphthyridyl, 2,3-dihydro[1,4]dioxino[2,3-b]pyridyl, 2,3-dihydro[1,4]dioxino[2,3-b]pryidyl, 3,4-dihydro-2H-1-oxa[4,6]diazanaphthalenyl, 4,5,6,7-tetrahydro-3H-imidazo[4,5-c]pyridyl, 6,7-dihydro[5,8]diazanaphthalenyl, 1,2,3,4-tetrahydro[1,5]napthyridinyl, 1,2,3,4-tetrahydro[1,6]napthyridinyl, 1,2,3,4-tetrahydro[1,7]naphthyridinyl, 1,2,3,4-tetrahydro[1,8]napthyridinyl, 1,2,3,4-tetrahydro[2,6]napthyridinyl, and the like, in which the bond to the parent moiety is through a non-aromatic carbon or nitrogen atom.

"Fused heterocyclylheteroaryl" means a radical derived from a fused heteroaryl and heterocyclyl as defined herein, by removal of a hydrogen atom from the heteroaryl portion. The fused heterocyclyl and heteroaryl is optionally substituted by one or more ring system substituents, wherein "ring system substituent" is as defined herein. Representative fused heterocyclylheteroaryl are as described herein for fused heteroarylheterocyclyl, except that the bond to the parent moiety is through an aromatic carbon atom.

"Aralkynyl" means an aryl-alkynylene- group wherein aryl and alkynylene are defined herein. Representative aralkynyl groups include phenylacetylenyl and 3-phenylbut-2-ynyl.

"Aryldiazo" means an aryl-N=N— group wherein aryl is as defined herein. Representative aryldiazo groups include phenyldiazo and naphthyldiazo.

"Arylcarbamoyl" means an aryl-NHCO— group, wherein aryl is as defined herein.

"Benzyl" means a phenyl-$CH_2$— group. Substituted benzyl means a benzyl group in which the phenyl ring is substituted with one or more ring system substituents. Representative benzyl include 4-bromobenzyl, 4-methoxybenzyl, 2,4-dimethoxybenzyl, and the like.

"Carbamoyl" means a group of formula $Y^{1a}Y^{2a}NCO$— wherein $Y^{1a}$ and $Y^{2a}$ are defined herein. Representative carbamoyl groups include carbamyl ($H_2NCO$—), dimethylaminocarbamoyl ($Me_2NCO$—), and the like.

"Carboxy" and "carboxyl" mean a HO(O)C— group (i.e. a carboxylic acid).

"Carboxyalkyl" means a HO(O)C-alkylene- group wherein alkylene is as defined herein. Representative carboxyalkyls include carboxymethyl and carboxyethyl.

"Cycloalkyloxy" means a cycloalkyl-O— group wherein cycloalkyl is as defined herein. Representative cycloalkyloxy groups include cyclopentyloxy, cyclohexyloxy, and the like.

"Diazo" means a bivalent —N=N— radical.

"Ethylenyl" means a —CH=CH— group.

"Halo" or "halogen" mean fluoro, chloro, bromo, or iodo.

"Heteroaralkenyl" means a heteroaryl-alkenylene- group wherein heteroaryl and alkenylene are as defined herein. Preferred heteroaralkenyls contain a lower alkenylene moiety. Representative heteroaralkenyl groups include 4-pyridylvinyl, thienylethenyl, pyridylethenyl, imidazolylethenyl, pyrazinylethenyl, and the like.

"Heteroaralkyl" means a heteroaryl-alkylene- group wherein heteroaryl and alkylene are as defined herein. Preferred heteroaralkyls contain a lower alkylene group.

Representative heteroaralkyl groups include thienylmethyl, pyridylmethyl, imidazolylmethyl, pyrazinylmethyl, and the like.

"Heteroaralkyloxy" means an heteroaralkyl-O-group wherein heteroaralkyl is as defined herein. A representative heteroaralkyloxy group is 4-pyridylmethyloxy.

"Heteroaralkyloxyalkenyl" means a heteroaralkyl-O-alkenylene- group wherein heteroaralkyl and alkenylene are as defined herein. A representative heteroaralkyloxyalkenyl group is 4-pyridylmethyloxyallyl.

"Heteroaralkyloxyalkyl" means a heteroaralkyl-O-alkylene- group wherein heteroaralkyl and alkylene are as defined herein. A representative heteroaralkyloxy group is 4-pyridylmethyloxyethyl.

"Heteroaralkynyl" means an heteroaryl-alkynylene- group wherein heteroaryl and alkynylene are as defined herein. Preferred heteroaralkynyls contain a lower alkynylene moiety. Representative heteroaralkynyl groups include pyrid-3-ylacetylenyl, quinolin-3-ylacetylenyl, 4-pyridylethynyl, and the like.

"Heteroaroyl" means an means a heteroaryl-CO— group wherein heteroaryl is as defined herein. Representative heteroaroyl groups include thiophenoyl, nicotinoyl, pyrrol-2-ylcarbonyl, pyridinoyl, and the like.

"Heteroaryldiazo" means an heteroaryl-N=N— group wherein heteroaryl is as defined herein.

"Heteroarylsulphonylcarbamoyl" means a heteroaryl-SO$_2$—NH—CO— group wherein heteroaryl is as defined herein.

"Heterocyclylalkyl" means a heterocyclyl-alkylene- group wherein heterocyclyl and alkylene are as defined herein. Preferred heterocyclylalkyls contain a lower alkylene moiety. A representative heteroaralkyl group is tetrahydropyranylmethyl.

"Heterocyclylalkyloxyalkyl" means a heterocyclylalkyl-O-alkylene group wherein heterocyclylalkyl and alkylene are as defined herein. A representative heterocyclylalkyloxyalkyl group is tetrahydropyranylmethyloxymethyl.

"Heterocyclyloxy" means a heterocyclyl-O— group wherein heterocyclyl is as defined herein. Representative heterocyclyloxy groups include quinuclidyloxy, pentamethylenesulfideoxy, tetrahydropyranyloxy, tetrahydrothiophenyloxy, pyrrolidinyloxy, tetrahydrofuranyloxy, 7-oxabicyclo[2.2.1]heptanyloxy, hydroxytetrahydropyranyloxy, hydroxy-7-oxabicyclo[2.2.1]heptanyloxy, and the like.

"Hydroxyalkyl" means an alkyl group as defined herein substituted with one or more hydroxy groups. Preferred hydroxyalkyls contain lower alkyl. Representative hydroxyalkyl groups include hydroxymethyl and 2-hydroxyethyl.

"N-oxide" means a

group.

"Phenoxy" means a phenyl-O— group wherein the phenyl ring is optionally substituted with one or more ring system substituents as defined herein.

"Phenylene" means a -phenyl- group wherein the phenyl ring is optionally substituted with one or more ring system substituents as defined herein.

"Phenylthio" means a phenyl-S— group wherein the phenyl ring is optionally substituted with one or more ring system substituents as defined herein.

"Pyridyloxy" means a pyridyl-O— group wherein the pyridyl ring is optionally substituted with one or more ring system substituents as defined herein.

"Ring system substituent" means a substituent which optionally replaces a hydrogen CH or NH constituent of an aromatic or non-aromatic ring system. Ring system substituents are selected from the group consisting of aryl, heteroaryl, aralkyl, aralkenyl, aralkynyl, heteroaralkyl, heteroaralkenyl, heteroaralkynyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, aryldiazo, heteroaryldiazo, amidino, $Y^{1a}Y^{2a}N$—, $Y^{1a}Y^{2a}N$-alkyl-, $Y^{1a}Y^{2a}NCO$— or $Y^{1a}Y^{2a}NSO_2$—, wherein $Y^{1a}$ and $Y^{2a}$ are independently hydrogen, alkyl, aryl, or aralkyl, or additionally, where the substituent is $Y^{1a}Y^{2a}N$— or $Y^{1a}Y^{2a}N$-alkyl-, then one of $Y^{1a}$ and $Y^{2a}$ is acyl or aroyl and the other of $Y^{1a}$ and $Y^{2a}$ is hydrogen, alkyl, aryl, and aralkyl. When a ring system is saturated or partially saturated, the "ring system substituent" further comprises methylene (H$_2$C=), oxo (O=) and thioxo (S=).

"Sulfamoyl" means a group of formula $Y^{1a}Y^{2a}NSO_2$— wherein $Y^{1a}$ and $Y^{2a}$ are as defined herein. Representative sulfamoyl groups are sulfamoyl (H$_2$NSO$_2$—) and dimethylsulfamoyl (Me$_2$NSO$_2$—)

PREFERRED EMBODIMENTS

The solid phase synthesis of N,N-disubstituted diazacycloakylcarboxy derivatives according to this invention is outlined in Scheme 1 wherein X, R$^1$, P$^1$, P$^2$, L$^1$ and L$^2$ are as defined herein. The groups R$^1$, L$^1$ and L$^2$ may be further substituted and may contain functional groups suitable for further chemical transformations while attached to the resin. It is understood that when these functional groups possess reactivity such that they could potentially interfere with the reactions described below, such functional groups should be suitably protected. For a comprehensive treatise on the protection and deprotection of common functional groups see T. H. Greene and P. G. M. Wuts, Protective Groups in Organic Synthesis, 2nd edition, John Wiley & Sons, New York (1991), the contents of which are hereby incorporated herein by reference.

Scheme 1

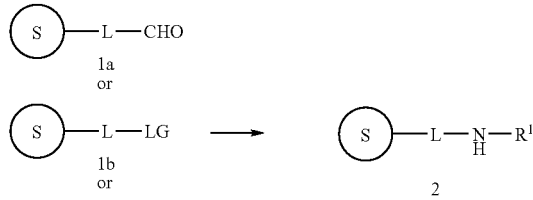

-continued

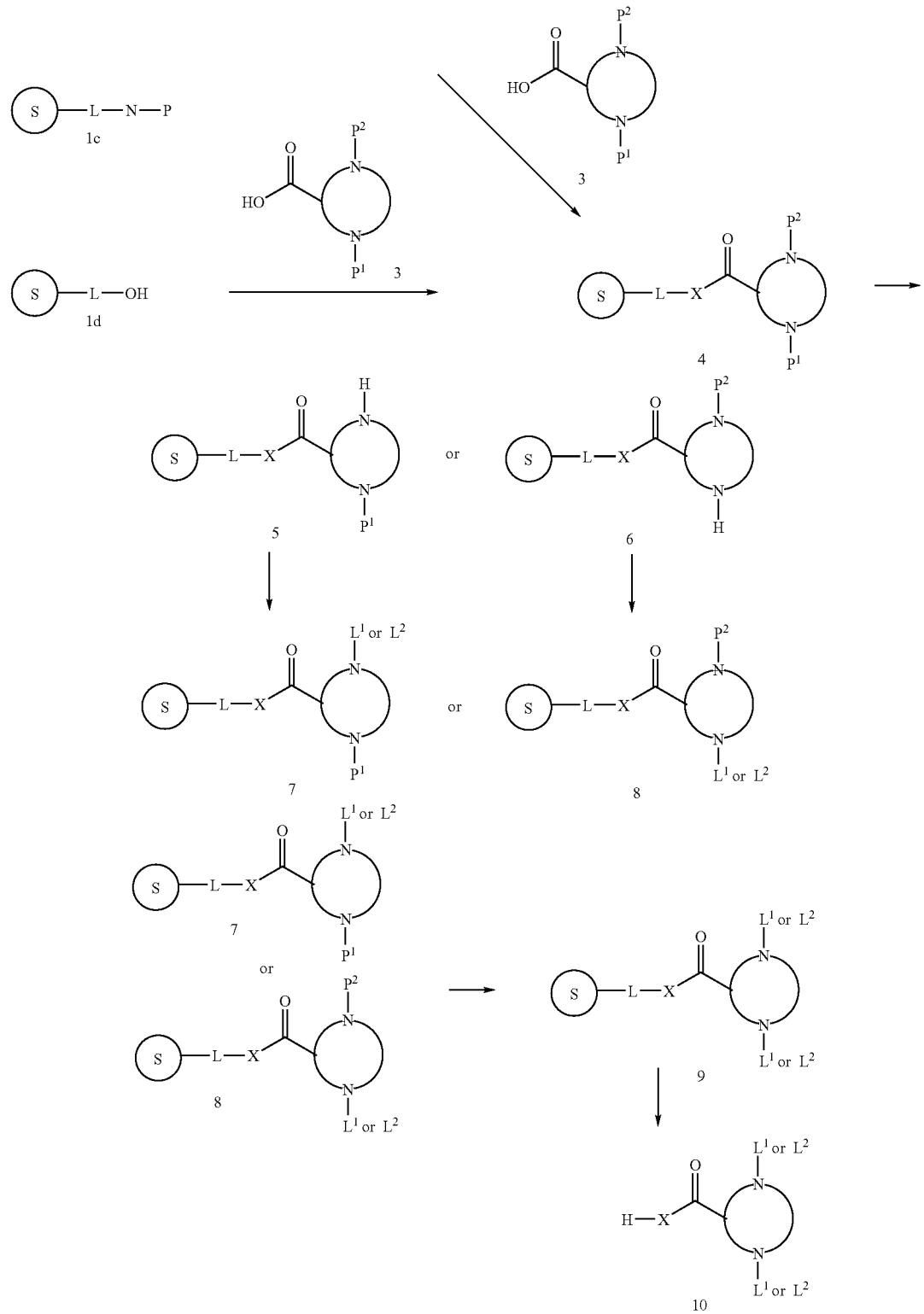

According to the foregoing Scheme 1, the amino resin 2 is prepared by reductive amination of a resin of formula 1a with an amine of formula $HNR^1$ using, for example, sodium triacetoxyborohydride, sodium cyanoborohydride or sodium borohydride in acetic acid/DMF, or by nucleophilic displacement of the leaving group LG from the resin of formula 1b with an amine of formula $HNR^1$ in the presence of base. Preferred leaving groups are Br and Cl.

Preferred resins suitable for reductive alkylation with an amine of formula $HNR^1$ include: 3,5-dimethoxy-4-formylphenoxymethyl-copoly(styrene-divinylbenzene)-resin (BAL resin), designated herein as

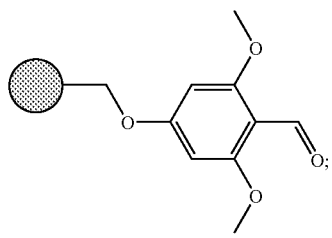

and 3-methoxy-4-formyl-phenoxymethyl-copoly(styrene-divinylbenzene)-resin, designated herein as

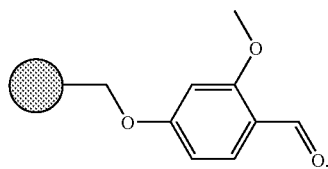

Preferred resins suitable for alkylation with an amine of formula $NHR^1$ include:

4-chloromethyl)phenoxymethyl-copoly(styrene-divinylbenzene)-resin, designated herein as

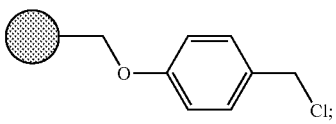

4-(4-bromomethyl)phenoxymethyl-copoly(styrene-divinylbenzene)-resin, designated herein as

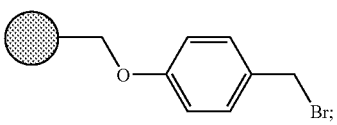

and 4-bromomethyl-3-nitro-benzamidomethyl-copoly(styrene-divinylbenzene)-resin (Baldwin, J. Am. Chem. Soc. 1995, 117, 5588), designated herein as

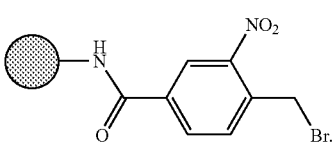

Resin 2 ($R^1$=H) can also be prepared from commercially available protected amino resin 1c by removal of the base labile nitrogen protecting group using for example piperidine in dimethyl formamide. Preferred protected amino-resins include:

Fmoc-Rink: amide resin 4-(2',4'-dimethoxyphenyl-Fmoc-aiminomethyl)-phenoxy resin available from Irori, USA designated herein as

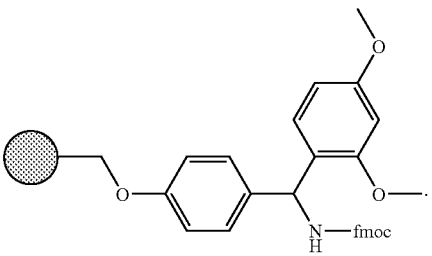

Coupling of the amino resin 2 with a N,N-diprotected diazacycloalkyl carboxylic acid derivative 3 in a suitable organic solvent such as dimethylformamide, dichloromethane, DMSO or THF using methods and reagents well-known in the art of amide bond formation results in formation of the resin-bound N,N-diprotected diazacycloalkyl carboxamide compound 4 (X=$NR^1$). Coupling times range from about 2 to about 12 hours, depending upon the amino resin and N,N-diprotected diazacycloalkyl carboxylic acid derivative to be coupled, activating agent, solvent and temperature. The coupling is accomplished at from about −10° C. to about 50° C., preferably at about ambient temperature. The carboxylic acid moiety is activated with an appropriate activating agent such as isopropyl chloroformate in the presence of N-methylpiperidine, diisopropylcarbodiimide (DIC) in the presence of 1-hydroxybenzotriazole (HOBT), bis(2-oxo-3-oxazolidinyl)-phosphonic chloride (BOP—Cl) in the presence of triethylamine, 2-(1H-benzotriazole-1-yl)-1.1.3.3-tetramethyluronium tetrafluoroborate (TBTU) in the presence of diisopropylethyl amine, N-hydroxysuccinimide in the presence of dicyclohexylcarbodiimide (DCC), bromo-tris-pyrrolidino-phosphonium hexafluorophosphate (Pybrop), and the like. Alternatively, the carboxylic acid moiety of the N,N-diprotected diazacycloalkyl carboxylic acid derivative 3 may be converted to a reactive derivative such as the acid chloride or fluoride or a symmetrical or mixed anhydride which is then reacted with the amino resin.

Resin bound N,N-diprotected diazabicycloakyl carboxamide compound 4 (X=O) is prepared by reaction of a hydroxymethyl resin (1d) with a N,N-diprotected diazacycloalkyl carboxylic acid derivative 3 in a suitable organic solvent such as dimethylformamide, dichloromethane, DMSO or THF using methods and reagents well-known in the art of ester bond formation. Preferred conditions include diisopropylcarbodiimide/dimethyl amino pyridine or the so called Yamaguchi method with 2,6-dichlorobenzoyl chloride and pyridine. Preferred hydroxymethyl resins include Wang resin (4-(4-hydroxymethyl)phenoxymethyl-copoly(styrene-divinylbenzene)-resin commercially available from Irori, USA designated herein as:

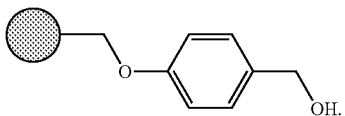

One of the nitrogen protecting groups $P^1$ and $P^2$ is then selectively removed by treatment of the resin-bound N,N-diprotected diazacycloalkyl carboxamide compound 4 with base or metal to form the resin-bound monoprotected diazacycloalkyl carboxy derivative 5 or 6.

Preferred base-labile nitrogen protecting groups include 9-fluorenylmethoxycarbonyl, 9-(2-sulfo)fluorenylmethoxycarbonyl and 9-(2,2-dibromo)-fluorenylmethoxycarbonyl, and the like, which are removed by treatment with, for example, piperidine, morpholine, dicyclohexylamine, dimethylaminopyridine, diisopropylethylamine, tetrabutylamonium fluoride, and the like in a suitable solvent such as DMF.

A more preferred base-labile nitrogen protecting group is 9-fluorenylmethoxycarbonyl which is removed by treatment with piperidine in DMF.

Preferred Metal-labile nitrogen protecting groups include allyloxycarbonyl, 1-isopropylallyloxycarbonyl, cinnamyloxycarbonyl and 4-nitrocinnamyloxycarbonyl, and the like which are removed by treatment with $Ni(CO)_4$, in DMF/$H_2O$, $Pd(Ph_3P)_4$ and $Bu_3SnH$ in acetic acid, $Pd(Ph_3P)_4$ and morpholine, $Pd(Ph_3P)_2Cl_2$ and $Bu_3SnH$ in 4-nitrophenol, $Pd_2(dba)_3$—$CHCl_3$ in $HCO_2H$, and the like.

A more preferred metal-labile nitrogen protecting group is allyloxycarbonyl which is removed by treatment with Pd(O), preferably $Pd(Ph_3P)_4$ and morpholine.

The group of formula $L^1$ or $L^2$ is then introduced into the resin-bound monoprotected diazacycloalkyl carboxy derivative 5 or 6 to form the resin-bound mono-N-acylated mono-N-protected diazacycloalkyl carboxy derivative 7 or 8. When $L^1$ or $L^2$ is a group of formula-$C(O)R^2$, —$C(O)$—$R^3$, —$C(O)O$—$R^2$, —$C(O)O$—$R^3$, —$C(O)N(4)$—$R^2$ or —$C(O)N(R^4)$-$R^3$ the acylation is accomplished using methods and reagents commonly used in the art of amide bond formation as described above for the conversion of 3 to 4. When $R^4$ is H, acylation is also accomplished using the isocyanate of formula $R^2NCO$ or $R^3NCO$.

When $L^1$ or $L^2$ is —$SO_2R^2$ or —$SO_2R^3$, sulfonylation is accomplished using a sulfonyl chloride of formula $ClSO_2R^2$ or $ClSO_2R^3$ in the presence of a base such as pyridine or N-methylmorpholine in an inert organic solvent such as dichloromethane.

The resin-bound mono-N-acylated mono-N-protected diazacycloalkyl carboxy derivative 7 or 8 is then converted to the resin-bound N,N-disubstituted diazacycloalkylcarboxy derivative 9 by removal of the other of $P^1$ and $P^2$ and introduction of the other of $L^1$ and $L^2$ using the procedures described above.

Treatment of the resin-bound N,N-disubstituted diazacycloalkyl carboxy derivative 9 with acid, preferably trifluoracetic acid in dichloromethane, results in formation of the N,N-disubstituted diazacycloalkylcarboxy derivatives 10.

In a more preferred aspect of the foregoing process

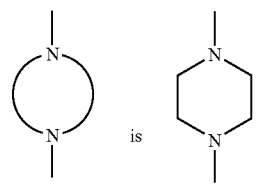

In another more preferred aspect of the foregoing process, $P^1$ is a base-labile nitrogen protecting group and $P^2$ is a Metal-labile nitrogen protecting group.

In a still more preferred aspect, the foregoing process comprises removing the base-labile nitrogen protecting group $P^1$ from a resin-bound diprotected diazacycloalkyl-2-carboxy derivative of formula

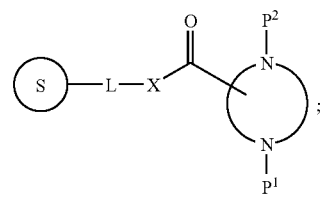

(2) introducing the group $L^1$, (3) removing the metal-labile nitrogen protecting group $P^2$, (4) introducing the group $L^2$ and (5) isolating the diazacycloalkyl-2-carboxy derivative.

An alternative solid phase synthesis of N,N-disubstituted diazacycloalkylcarboxy derivatives is outlined in Scheme 2 wherein $Z^1$, $Z$, $R^5$, $R^6$, $R^7$, $R^8$, $R^9P^3$ and $L^3$ are as defined herein.

Scheme 2

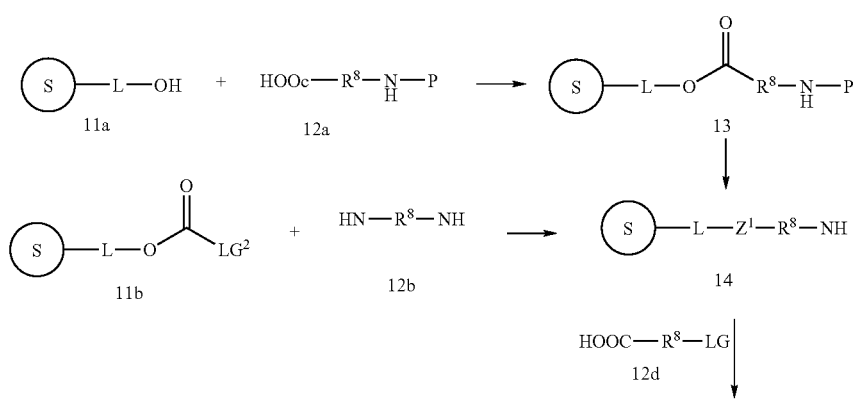

-continued

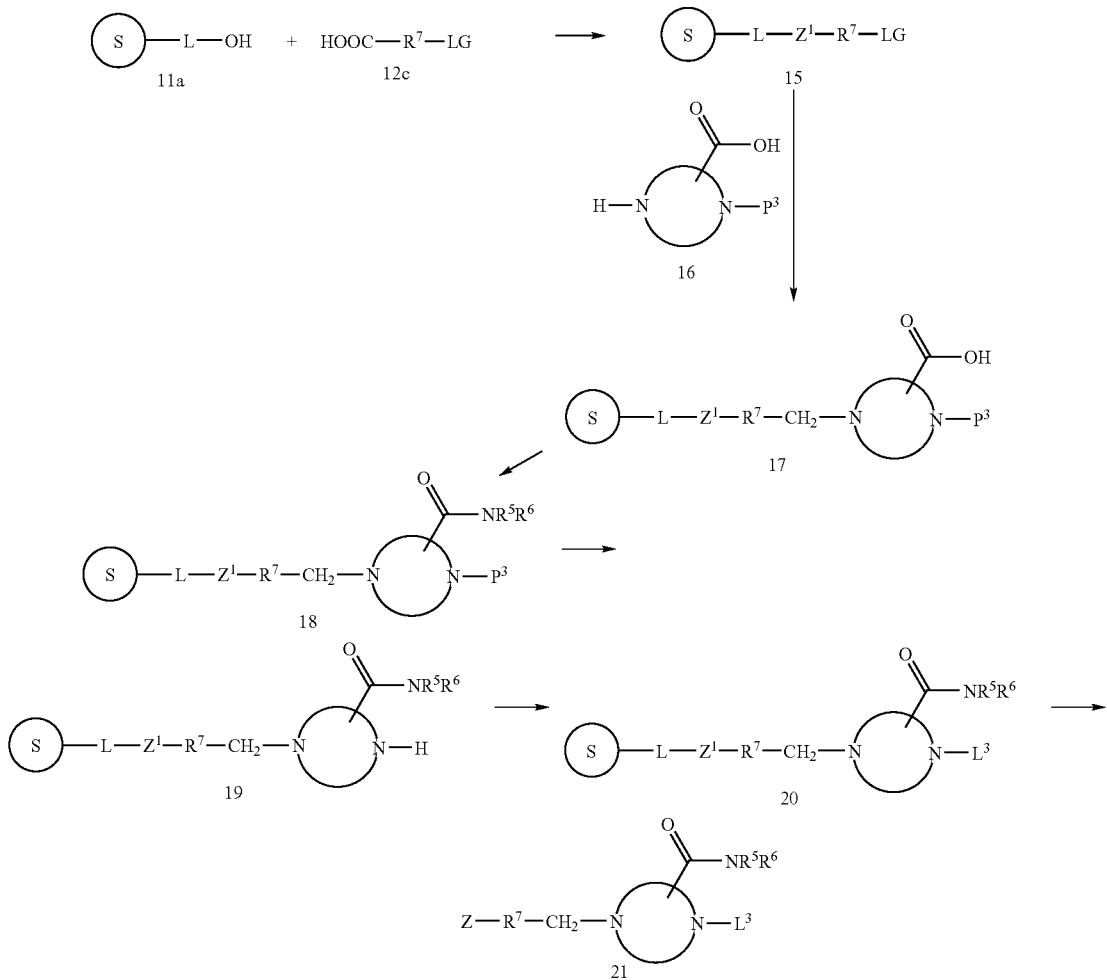

According to the foregoing scheme 2, three methods can be used to prepare resin 15 ($Z^1$ is O—C(O)— or O—C(O)—$NR^{13}$—, LG is a leaving group). Coupling of the hydroxyresin 11a with the carboxylic acid derivative 12c or the protected amino-acid 12a (P is a nitrogen protecting group) using standard conditions for ester bond formation results in the formation of 13 or 15. Preferred conditions include coupling of an acid chloride with the hydroxy resin, the so-called Yamaguchi Method (2,6 dichlorobenzoyl chloride) and diisopropylcarbodiimide/4-dimethylaminopyridine.

A preferred hydroxy resin is Wang resin (4-(4-hydroxymethyl)phenoxymethyl-copoly(styrene-divinylbenzene)-resin.

The nitrogen protecting group of 13 is removed using standard deprotection conditions resulting in the formation of free amine 14 ($Z^1$ is O—C(O)—). Preferred nitrogen protecting group include include 9-fluorenylmethoxycarbonyl which is removed by treatment with, for example, piperidine, morpholine, dicyclohexylamine.

Coupling of the carbonate resin 11b ($LG^2$ is a leaving group) with a symmetrical diamine 12b in an organic solvent such as dimethyl formamide or dichloromethane results in the formation of 4 ($Z^1$ is O—C(O)—$NR^{13}$). A preferred carbonate resin is p-Nitrophenyl carbonate Wang (4-(4-(4-nitrophenylcarbonate)hydroxymethyl)phenoxymethyl-copoly(styrene-divinylbenzene)-resin available from Novabiochem, USA designated herein as:

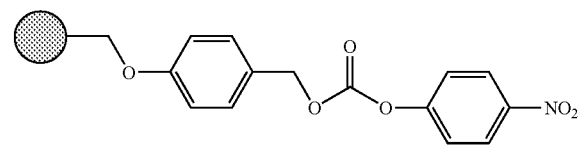

Amide bond between the free amine resin 14 and carboxylic acid 12c are formed using the conditions described in Scheme 1 above for the conversion of 2 to 3.

Alkylation of 15, wherein LG is a leaving group, with the mono-N-protected diazacycloalkyl carboxylic acid compound 16 results in formation of the resin-bound N-protected diazacycloalkyl carboxylic acid compound 17. Alkylation is typically accomplished in the presence of a base such as diisopropylethylamine in a suitable organic solvent such as DMF at a temperature of from about ambient temperature to about 100° C. Preferred leaving groups are Cl and Br. Optionally, a catalyst such as potassium iodide may be added to the reaction mixture.

The resin-bound N-protected diazacycloalkyl carboxylic acid compound 17 is then converted to the resin-bound N-protected diazacycloalkyl carboxamide compound 18 by reaction with the amine $NHR^5R^6$ using the conditions described in Scheme 1 above for the conversion of 2 to 3. More preferred conditions are reaction of the resin bound carboxylic acid with pentafluorophenol and diisopropylcarbodiimide, followed by reaction with the amine in dimethyl formamide.

The nitrogen protecting group P3 is then removed to form the resin-bound carboxy derivative 19.

Preferred nitrogen protecting groups are base-labile nitrogen protecting groups and metal-labile nitrogen protecting groups.

More preferred nitrogen protecting groups are metal-labile nitrogen protecting groups selected from allyloxycarbonyl, 1-isopropylallyloxycarbonyl, cinnamyloxycarbonyl and 4-nitrocinnamyloxycarbonyl and base-labile nitrogen protectings group selected from 9-fluorenylmethoxycarbonyl, 9-(2-sulfo)fluorenylmethoxycarbonyl and 9-(2,2-dibromo)-fluorenylmethoxycarbonyl.

Still more preferred nitrogen protecting groups are allyloxycarbonyl and 9-fluorenylmethoxycarbonyl.

A still yet more preferred nitrogen protecting group is allyloxycarbonyl.

The group $L^3$ is then added using the conditions described in Scheme 1 above to form the resin-bound N-substituted diazacycloalkyl carboxy derivative 20. Treatment of 20 with acid as described in Scheme 1 above provides the N,N-disubstituted diazacycloalkyl carboxy derivative 21.

The preparation of hydantoin compounds of N-aryl hydantoin compounds of formula 23 wherein $R^{14}$, $R^{17}$ and $L^4$ are as defined herein is described in Scheme 3.

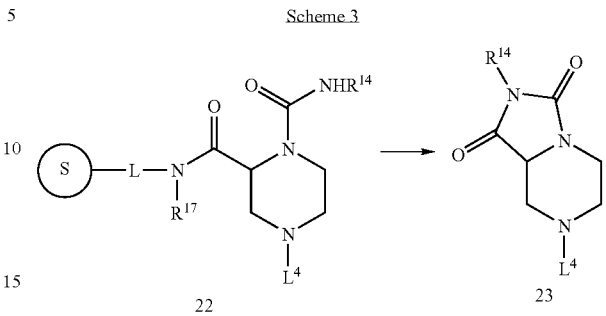

Scheme 3

As shown in Scheme 3, treatment of the resin-bound aryl carbamate compound 22, prepared as described in Scheme 1 above, with acid, preferably trifluoroacetic acid, results in cyclization and cleavage from the resin to form the hydantoin 23.

The process of this invention is especially useful for the rapid synthesis of combinatorial libraries containing a large number of diazacycloalkylcarboxy derivative.

The synthesis of a representative library is of N,N-disubstituted diazacycloalkylcarboxy derivatives using the process of this invention is outlined in Scheme 4.

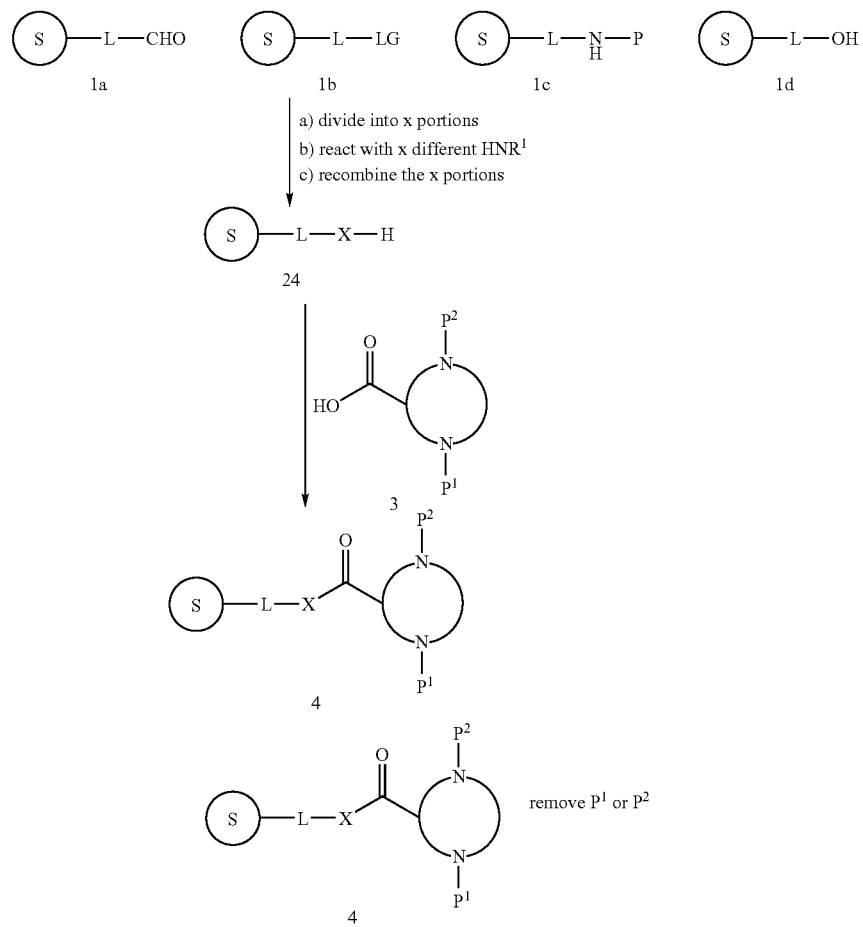

Scheme 4

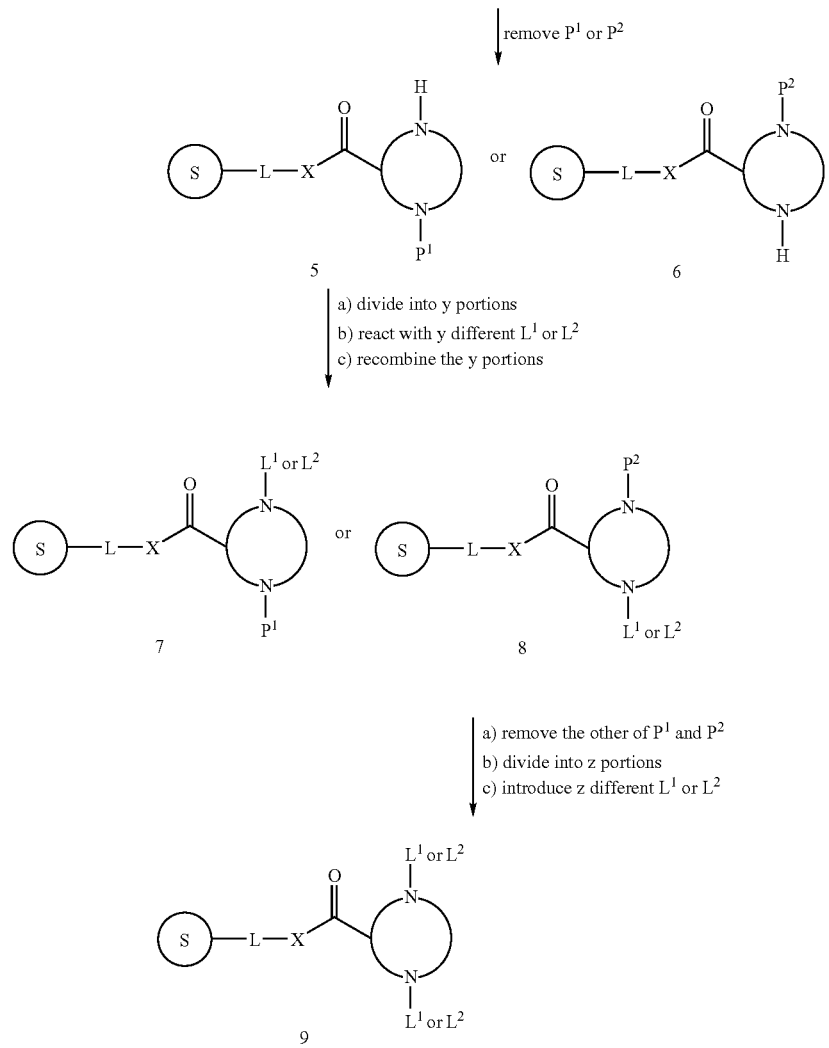

As shown in Scheme 4, a single portion of resin 1a is divided into x smaller portions containing approximately equal amounts of resin. Each portion of resin 1a is then reductively aminated as described in Scheme 1 above with a different amine of formula $HNR^1$, where x corresponds to the total number of different amines. Alternatively, a resin of formula 1b may be reacted with x different nucleophilic amines of formula $HNR^1$ as described in Scheme 1 above to form x portions of resin 24 (X is $HNR^1$) each of which contains a different $R^1$. One portion of resin 1c is deprotected to form 24 (X is NH2) and one portion of resin 1d is left unreacted to form 24 (X=OH). The group X which is substituted with O or $NR^1$ is referred to herein as the first combinatorial position. The x+2 portions are then recombined into a single portion and one of the protecting groups $P^1$ or $P^2$ is then removed as described in Scheme 1 above to form a mixture of resin-bound monoprotected diazacycloalkylcarboxy derivatives 5 or 6 containing x+2 different groups at the first combinatorial position.

The mixture of resin-bound monoprotectedcarboxy derivatives 5 or 6, is then divided into y portions, y different groups $L^1$ or $L^2$ are introduced at the second combinatorial position using the procedures described in Scheme 1 above and the y portions are recombined to form a single portion, referred to herein as the second combinatorial mixture, comprising a mixture of resin-bound N-acylated-mono-N-protected diazacycloalkylcarboxy derivatives 7 or 8 containing all possible combinations of the x+2 $R^1$ groups and y $L^1$ or $L^2$ groups.

The other of $P^1$ and $P^2$ is then removed from the second combinatorial mixture, the resulting mixture of resin-bound N-acylated diazacycloalkylcarboxy derivative is divided into z portions and z different groups $L^1$ or $L^2$ are introduced into the third combinatorial position as described above to form z portions of resin-bound N,N-disubstituted diazacycloalkylcarboxy derivatives 9.

The N,N-disubstituted diazacycloalkylcarboxy derivatives 9 are then cleaved from the resin as described in Scheme 1 above to give a library of N,N-disubstituted diazacycloalkylcarboxy derivatives containing all possible combinations of groups at each of the combinatorial positions. Using the procedure described above, a library of 10,000 compounds may be readily prepared from reagents corresponding to 25 $R^1$ groups, 20 $L^1$ groups and 20 $L^2$ groups.

The progress of the combinatorial synthesis may be monitored by use of identifier tags. "Identifier tag" denotes a physical attribute that provides a means whereby one can identify a chemical reaction. The identifier tag serves to record a step in a series of reactions used in the synthesis of a chemical library. The identifier tag may have any recognizable feature, including for example: a microscopically or otherwise distinguishable shape, size, mass, color, optical density, etc.; a differential absorbance or emission of light; chemical reactivity; magnetic or electronic properties; or any other distinctive mark capable of encoding the required information, and decipherable at the level of one (or a few) molecules. Identifier tags can be coupled to the solid support. Alternatively, the "identifier tag" can be coupled directly to the compound being synthesized, whether or not a solid support is used in the synthesis. In the latter embodiment, the identifier tag can conceptually be viewed as also serving as the "support" for synthesis.

In a preferred embodiment, a radio-frequency identifier tag is associated with each compound in the library. In a library preparation monitored by use of radio-frequency tags, each compound is made in a polypropylene container with mesh side walls (MicroKan™, available from Irori, La Jolla, Calif., USA) in which resin and a radio frequency tags are placed. The overall synthesis is programmed in a computer which incorporate a scanning station to track the RF-tags. As the MicroKans™ are scanned for the first time, a library member is assigned to each code. Along with this assignment the MicroKans™ are directed toward the vessel for the first combinatorial step. They are then reacted as a batch with the first set of combinatorial reagents. After the first combinatorial reaction, the MicroKans™ are pooled, and the scanner is then used to direct the cans into the vessels corresponding to their second combinatorial step. And so on for all the combinatorial steps. At the end of the synthesis, the final scan assigns a plate number and a well location to each compound in the library.

It is to be understood that this invention covers all appropriate combinations of the particular and preferred groupings referred to herein.

The foregoing may be better understood by reference to the following examples, which are presented for illustration and are not intended to limit the scope of this invention.

EXAMPLE 1

Preparation of BAL Resin

4-Hydroxy-2,6-dimethoxybenzaldehyde (127.53 g, 700.0 mmol) is dissolved in anhydrous dimethylformamide (3.0 L). Sodium hydride (26.4 g of 60% sodium hydride in oil, 660.0 mmol) is added slowly in portions to the stirring solution at ambient temperature under a flow of nitrogen gas. After the sodium hydride addition is complete, the reaction is stirred at ambient temperature for 30 minutes. Chloromethylpolystyrene resin (100.0 g of 2.0 mmol/g loaded 150–300 um beads from Polymer Laboratories) is added to the ruby red solution and the resulting suspension is stirred at ambient temperature for 30 minutes under nitrogen. The nitrogen line is removed and replaced with a needle to vent the reaction. The reaction flask is placed in an incubator shaker and mixed for two days at 50° C. The reaction flask is removed from the oven, cooled in an ice bath, and water (500 ml) is added. The resin is filtered off and washed with 1:1 dimethylformamide/methanol (3×), dimethylformamide (3×), dichloromethane (3×) and methanol (3×). The resin is then placed in a vacuum oven an dried at ambient temperature for about 2 days. The resin loading is determined to be approximately 1.0 mmol/g.

EXAMPLE 2

Preparation of 1-Alloc-4-Fmoc-piperazine-2-Carboxylic Acid

Step 1: 4-Boc-piperazine-2-Carboxylic Acid.

piperazine-2-carboxylic acid dihydrochloride (10.0 g, 49.23 mmol) is dissolved in 1:1 dioxane/water (320 ml). 50% Aqueous sodium hydroxide is added to bring the pH to 11. BOC-ON (2-(tert-butoxycarbonyloxyimino)-2-phenylacetonitrile), (15.59 g, 63.32 mmol) is dissolved in dioxane (80 ml) and added dropwise while maintaining the pH at 11 with 50% aqueous sodium hydroxide. The reaction is stirred overnight at ambient temperature. The reaction mixture is then extracted with diethyl ether (5×250 ml) and acidified to pH 2 with concentrated hydrochloric acid. The di-Boc compound is then extracted out with ethyl acetate (4×200 ml) and the acidic aqueous solution containing the desired mono-Boc product is then taken on in the synthesis.

Step 2: 1-Alloc-4-Boc-piperazine-2-Carboxylic Acid.

The aqueous acidic solution of 4-Boc-piperazine-2-carboxylic acid prepared above is basified to pH 9.5 with 50% sodium hydroxide solution. This solution is cooled in an ice bath and allyl chloroformate (6.1 ml, 57.10 mmol) is added portionwise by syringe while maintaining the pH at 9.5 with 50% sodium hydroxide solution. The ice bath is removed after the addition is complete and the reaction mixture is warmed to ambient temperature with stirring overnight. The basic solution is then extracted with diethyl ether (4×), acidified to pH 1.0 with concentrated hydrochloric acid and extracted with ethyl acetate (4×). The combined ethyl acetate extracts are dried over anhydrous magnesium sulfate, filtered and concentrated. The resulting oil is placed on a high vacuum line to dry. The title compound (9.18 g) is obtained as a viscous yellow oil.

Step 3: 1-Alloc-piperazine-2-Carboxylic Acid.

1-Alloc-4-Boc-piperazine-2-carboxylic acid prepared above (9.10 g) is dissolved in dichloromethane (100 ml) and trifluoroacetic acid (100 ml) is added. The reaction mixture is stirred at ambient temperature for 2.5 hours. It is then concentrated and the residual trifluoroacetic acid is azeotroped off with toluene. The resulting white solid is dried on a high vacuum line to provide the title compound (8.68 g, 94% pure by HPLC analysis).

Step 4: 1-Alloc-4-Fmoc-piperazine-2-Carboxylic Acid.

1-Alloc-piperazine-2-carboxylic acid (8.60 g, 26.20 mmol) is dissolved in water (70 ml). Sodium carbonate (6.94 g, 65.50 mmol) is added slowly with stirring. Dioxane (40 ml) is added and the reaction mixture is cooled in an ice bath. 9-Fluorenylmethyl chloroformate (6.76 g, 26.20 mmol) is added all at once and the reaction mixture is stirred at 0° C. for 5 hours. The ice bath is removed and the reaction mixture is warmed to ambient temperature with stirring overnight. The reaction mixture is then diluted with water (400 ml) and extracted with diethyl ether (4×). The aqueous solution is acidified to pH 1.0 with concentrated hydrochloric acid and extracted with ethyl acetate (4×). The combined ethyl acetate extracts are dried over anhydrous magnesium sulfate, filtered and concentrated. The resulting oil is dried under high vacuum line to provide the title compound (12.66 g, 96% pure by HPLC analysis, 59% overall yield from piperazine-2-carboxylic acid) as a viscous yellow oil.

EXAMPLE 3

Preparation of N-butyl 1-(3,4-dichlorobenzoyl)-4-phenylsulfonylpiperazine-2-carboxamide

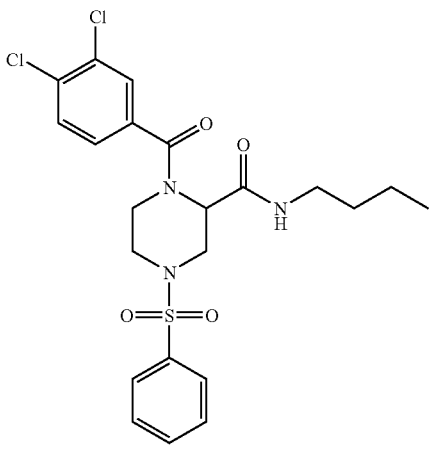

Step 1: Reductive Amination on the BAL Resin.

BAL resin is swelled in a 1% acetic acid in dimethylformamide solution. Butylamine (20.0 mmol) and sodium triacetoxyborohydride (20.0 mmol) are added sequentially. The reaction mixture is stirred at ambient temperature for 6.5 hours. The liquid is then removed and the resin is washed with 1:1 dimethylformamide/methanol (2×), dimethylformamide (2×), dichloromethane (3×) and diethyl ether (1×) and dried overnight with a stream of nitrogen gas.

Step 2: Acylation with 1-Alloc-4-fmoc-piperazine-2-Carboxylic Acid.

Dimethylformamide is added to swell the resin prepared in step 1 above. 1-Alloc-4-fmoc-piperazine-2-carboxylic acid (180.0 mmol) is dissolved in dimethylformamide and added to the resin. O-Benzotriazol-1-yl-N,N,N',N'-tetramethyluronium hexafluorophosphate (180.0 mmol) and diisopropylethylamine (360.0 mmol) are then added sequentially. The reaction mixture is stirred at ambient temperature for 6.5 hours. The liquid is removed and the resin is washed with dimethylformamide (3×), dichloromethane (3×) and diethyl ether (1×) and dried overnight with a stream of nitrogen gas.

Step 3: Fmoc Deprotection.

Dimethylformamide and piperidine are added to the above resin prepared in step 2 above and the reaction mixture is stirred at ambient temperature for 3.5 hours. The liquid is then removed and the resin is washed with dimethylformamide (3×), dichloromethane (3×), and diethyl ether (1×) and dried overnight with a stream of nitrogen gas.

Step 4: Sulfonamide Formation.

The resin prepared is step 3 above is swelled in anhydrous dichloromethane. N-Methylmorpholine (50.0 mmol) and benzenesulfonyl chloride (50.0 mmol) are then added sequentially. The reaction mixture is stirred overnight at ambient temperature. The liquid is then removed and the resin is washed with dimethylformamide (2×), tetrahydrofuran (1×), dichloromethane (2×), and diethl ether (1×) and dried overnight with a stream of nitrogen gas.

Step 5: Alloc Deprotection.

Tetrahydrofuran, dimethylsulfoxide and 0.5N hydrochloric acid (2:2:1) are added to the resin prepared in step 4 above. The reaction flask is flushed with nitrogen and Pd(Ph$_3$P)$_4$ (6.98 mmol) and morpholine (2500 mmol) are added sequentially. The reaction mixture is stirred overnight under a flow of nitrogen gas. The liquid is then removed and the resin is washed with tetrahydrofuran (2×), sodium diethyldithiocarbamate [0.02M in dimethylformamide] (2×), dimethylformamide (2×), 0.5% diisopropylethylamine in dichloromethane (1×), dichloromethane (3×) and diethyl ether (1×) and dried overnight with a stream of nitrogen gas.

Step 6: Acylation with Carboxylic Acid.

The resin is prepared in step 5 above is swelled in 1-methyl-2-pyrrolidinone and 3,4-dichlorobenzoic acid (20.0 mmol) and 1-[3-(dimethylamino)propyl]-3-ethylcarbodiimide hydrochloride (20.0 mmol) are added sequentially. The reaction mixture is stirred overnight at ambient temperature. The liquid is then removed and the resin is washed with dimethylformamide (2×), dichloromethane (3×), and diethyl ether (1×) and dried overnight with a stream of nitrogen gas.

Step 7: Cleavage.

The resin prepared in step 6 above is cleaved with 50% trifluoroacetic acid in dichloromethane for one hour to yield the title compound (99.5% pure by ELSD). Expected product MW is 497. Observed product MW is 497.

EXAMPLE 4

Preparation of N-butyl 1-phenylsulfonyl-4-(tert-butylacetyl)piperazine-2-carboxamide

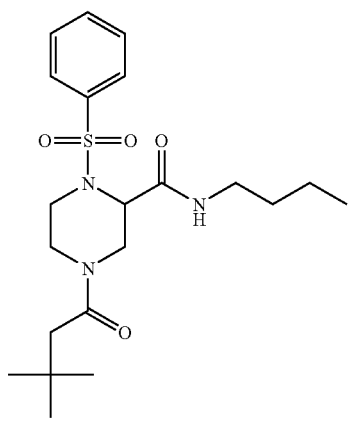

Step 1: Reductive Amination on the BAL Resin.

BAL resin is swelled in a 1% acetic acid in dimethylformamide solution. Butylamine (20.0 mmol) and sodium triacetoxyborohydride (20.0 mmol) are added sequentially. The reaction mixture is stirred at ambient temperature for 6.5 hours. The liquid is then removed and the resin is washed with 1:1 dimethylformamide/methanol (2×), dimethylformamide (2×), dichloromethane (3×) and diethyl ether (1×) and dried overnight with a stream of nitrogen gas.

Step 2: Acylation with 1-Alloc-4-Fmoc-piperazine-2-Carboxylic Acid.

Dimethylformamide is added to swell the resin prepared in step 1 above. 1-Alloc-4-fmoc-piperazine-2-carboxylic acid (180.0 mmol) is dissolved in dimethylformamide and added to the resin. O-Benzotriazol-1-yl-N,N,N',N'-tetramethyluronium hexafluorophosphate (180.0 mmol) and diisopropylethylamine (360.0 mmol) are then added sequentially. The reaction mixture is stirred at ambient temperature for 6.5 hours. The liquid is removed and the resin is washed with dimethylformamide (3×), dichloromethane (3×) and diethyl ether (1×) and dried overnight with a stream of nitrogen gas.

Step 3: Fmoc Deprotection.

Dimethylformamide and piperidine are added to the above resin prepared in step 2 above and the reaction mixture is stirred at ambient temperature for 3.5 hours. The liquid is then removed and the resin is washed with dimethylformamide (3×), dichloromethane (3×), and diethyl ether (1×) and dried overnight with a stream of nitrogen gas.

Step 4: Acylation with Carboxylic Acid.

The resin prepared in step 3 above is swelled in 1-methyl-2-pyrrolidinone. Tert-butyl acetic acid (20.0 mmol) and 1-[3-(dimethylamino)propyl]-3-ethylcarbodiimide hydrochloride (20.0 mmol) are added sequentially and the reaction mixture is stirred overnight at ambient temperature. The liquid is then removed and the resin is washed with dimethylformamide (2×), dichloromethane (3×) and diethyl ether (1×) and dried overnight with a stream of nitrogen gas.

Step 5: Alloc Deprotection.

Tetrahydrofuran, dimethylsulfoxide and 0.5N hydrochloric acid (2:2:1) are added to the resin prepared in step 4 above. The reaction flask is flushed with nitrogen and Pd(Ph$_3$P)$_4$ (6.98 mmol) and morpholine (2500 mmol) are added sequentially. The reaction mixture is stirred overnight under a flow of nitrogen gas. The liquid is then removed and the resin is washed with tetrahydrofuran (2×), sodium diethyldithiocarbamate [0.02M in dimethylformamide] (2×), dimethylformamide (2×), 0.5% diisopropylethylamine in dichloromethane (1×), dichloromethane (3×) and diethyl ether (1×) and dried overnight with a stream of nitrogen gas.

Step 6: Sulfonamide Formation.

The resin prepared in step 5 above is swelled in anhydrous dichloromethane and N-methylmorpholine (50.0 mmol) and benzene sulfonyl chloride (50.0 mmol) are added sequentially. The reaction mixture is stirred overnight at ambient temperature. The liquid is removed and the resin is washed with dimethylformamide (2×), tetrahydrofuran (1×), dichloromethane (2×), and diethyl ether (1×) and dried overnight with a stream of nitrogen gas.

Step 7: Cleavage.

The resin is cleaved with 50% trifluoroacetic acid in dichloromethane for one hour to yield the title compound (93.4% pure by ELSD). Expected product MW is 423. Observed product MW is 423.

EXAMPLE 5

Preparation of N-2-(4-benzenesulfonamido)ethyl 1-(p-toluenesulfonyl)-4-(4-carboxymethylphenylmethyl)piperazine-2-carboxamide

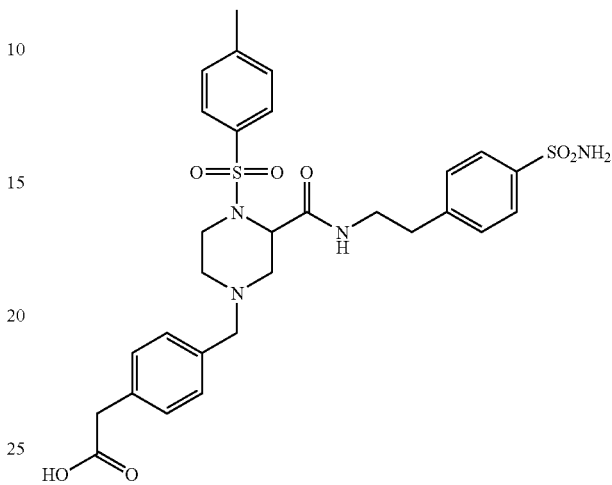

Step 1: Loading of Bromo-acid (Yamaguchi Method).

4-(Bromomethyl)phenylacetic acid (529 mg, 2.34 mmol) is poured into 5 ml of dimethylformamide. Pyridine (170 ul, 2.125 mmol) and 2,6-dichlorobenzoylchloride (301ul, 2.125 mmol) are then added and the mixture is shaken for 1 hour. Wang resin (loading 1.7 mmol/g) is added and the mixture is shaken overnight. The liquid is then removed and the resin is washed with dimethylformamide (3×), tetrahydrofuran (3×), dichloromethane (3×), and diethyl ether (2×) and dried in vacuo.

Step 2: Alkylation with 1-Alloc-2-carboxypiperidine.

The resin prepared in step 1 above (4.6 g, 7.82 mmol) is suspended in dimethylformamide (15 ml) and 1-Alloc-2-carboxypiperidine trifluoroacetic acid salt (2.71 g, 23.4 mmol), potassium iodide (458 mg, 23.4 mmol) and diisopropylethylamine (2.89 ml, 45 mmol) are added. This reaction mixture is heated overnight at 80°. The liquid is removed and the resin is washed with dimethylformamide (3×), tetrahydrofuran (3×), dichloromethane (3×), and diethyl ether (1×).

Step 3: Amide Bond Formation.

The resin prepared in step 2 is swelled in dimethylformamide (300 ml). Diisopropylcarbodiimide (4.79 ml) and pentafluorophenol (5.63 g) are added and the reaction mixture is stirred at ambient temperature for for two hours. The liquid is removed and the resin is washed with dimethylformamide (2×). The resin is again suspended in dimethylformamide(300 ml) and 4-(2-aminoethyl)benzenesulfonamide (10 eq., 20.4 mmol) is added and the reaction mixture is stirred at ambient temperature overnight. The liquid is removed and the resin is washed with dimethylformamide (3×), tetrahydrofuran (3×), dichloromethane (3×), and diethyl ether (1×) and dried overnight with a stream of nitrogen.

Step 4: Alloc Deprotection.

Tetrahydrofuran, dimethylsulfoxide, and 0.5N hydrochloric acid (2:2:1) are added to the resin prepared in step 3. The reaction flask is flushed with nitrogen and Pd(Ph$_3$P)$_4$ (8.06 g, 6.98 mmol) and morpholine (218 ml, 2500 mmol) are added sequentially. The reaction mixture is stirred overnight under a flow of nitrogen gas. The liquid is then removed and the resin is washed with tetrahydrofuran (2×), sodium diethyldithiocarbamate (0.02M in dimethylformamide) (2×), dimethylformamide (2×), 0.5% diisopropylethylamine in dichloromethane (1×), dichloromethane (3×) and diethyl ether (1×) and dried overnight with a stream of nitrogen gas.

Step 5: Sulfonamide Formation.

The resin prepared in step 4 is swelled in a mixture of dichloromethane:pyridine (1350 ml dichloromethane: 150 ml pyridine). p-Toluenesulfonyl chloride (10 eq, 42.5 mmol) is added and the reaction mixture is stirred overnight at ambient temperature. The liquid is then removed and the resin is washed with dimethylformamide(3×), tetrahydrofuran(2×), dichloromethane(3×), and ether (1×) and dried overnight with a stream of nitrogen gas.

Step 6: Cleavage.

The resin prepared in step 5 is cleaved with 50% trifluoroacetic acid in dichloromethane for one hour to yield the title compound (85.8% pure by ELSD). Expected product MW is 614. Observed product MW is 614.

EXAMPLE 6

Preparation of N-3-(pyrrolidin-2-one-1-yl)propyl 1-(p-toluenesulfonyl)-4-[2-(2-carboxypyrrolidinyl) ethan-2-one-1-yl]piperazine-2-carboxamide

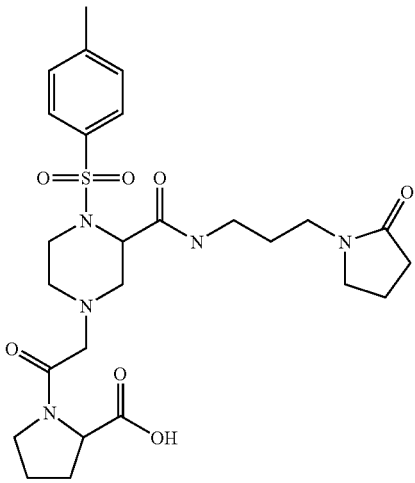

Step 1: Loading of Fmoc-Amino Acid.

Wang resin (1150 mg, 0.255 mmol) is suspended in dichloromethane (2 ml). Fmoc-proline (5 eq, 1.25 mmol) is added, followed by diisopropylcarbodiimide (200 ul, 1.25 mmol) and 4-dimethylaminopyridine (6.4 mg, 0.052 mmol) and the reaction mixture is shaken overnight. The liquid is removed and the resin is washed with dichloromethane (2×), dimethylformamide (3×), tetrahydrofuran (3×), dichloromethane (3×), and diethyl ether (2×) and dried in vacuo.

Step 2: Removal of fmoc Group.

The resin prepared in step 1 (150 mg, 0.255 mmol) is suspended in a mixture of piperidine and dimethylformamide (1:1) and the reaction mixture is shaken overnight. The liquid is removed and the resin is washed with dichloromethane (2×), dimethylformamide (3×), tetrahydrofuran (3×), dichloromethane (3×) and diethyl ether (2×) and dried in vacuo.

Step 3: Coupling with Bromoacetic Acid.

The resin from step 2 (1100 mg, 0.17 mmol) is suspended in dichloromethane (110 ml). Bromoacetic acid (1.7 mmol) and diisopropylcarbodiimide (267 ul, 1.7 mmol) are added and the reaction mixture is shaken overnight. The liquid is removed and the resin is washed with dichloromethane (2×), dimethylformamide (3×), tetrahydrofuran (3×), dichloromethane (3×) and diethyl ether (2×) and dried in vacuo.

Step 4: Alkylation with 1-alloc-2-carboxy-piperidine.

The resin prepared in step 3 (4.6 g, 7.82 mmol) is suspended in dimethylformamide (15 ml). 1-Alloc-2-carboxy-piperidine.trifluoroacetic acid salt (2.71 g, 23.4 mmol), potassium iodide (458 mg, 23.4 mmol) and diisopropylethylamine (2.89 ml, 45 mmol) are added and the reaction mixture is heated overnight at 80° C. The liquid is removed and the resin is washed with dimethylformamide (3×), tetrahydrofuran (3×), dichloromethane (3×), and diethyl ether (1×).

Step 5: Amide Bond Formation.

The resin prepared in step 4 is swelled in dimethylformamide (300 mL). Diisopropylcarbodiimide (4.79 ml) and pentafluorophenol (5.63 g) are added and the reaction mixture is stirred at ambient temperature for two hours. The liquid is removed and the resin is washed with dimethylformamide (2×). The resin is again suspended in dimethylformamide(300 ml) and N-(3-aminopropyl)-2-pyrrolidinone (10 eq., 20.4 mmol) is added. The reaction mixture is stirred at ambient temperature overnight. The liquid is then removed and the resin is washed with dimethylformamide (3×), tetrahydrofuran (3×), dichloromethane (3×) and diethyl ether (1×) and dried overnight with a stream of nitrogen.

Step 6: Alloc Deprotection.

Tetrahydrofuran, dimethylsulfoxide, and 0.5N hydrochloric acid (2:2:1) are added to the resin prepared in step 5. The reaction flask is flushed with nitrogen. Pd(Ph$_3$P)$_4$ (8.06 g, 6.98 mmol) and morpholine (218 ml, 2500 mmol) are added sequentially and the reaction mixture is stirred overnight under a flow of nitrogen gas. The liquid is then removed and the resin is washed with tetrahydrofuran (2×), sodium diethyldithiocarbamate (0.02M in dimethylformamide) (2×), dimethylformamide (2×), 0.5% diisopropylethylamine in dichloromethane (1×), dichloromethane (3×) and diethyl ether (1×) and dried overnight with a stream of nitrogen gas.

Step 7: Sulfonamide Formation.

The resin prepared in step 6 is swelled in dichloromethane/pyridine (1350 ml dichloromethane: 150 ml pyridine). P-toluenesulfonyl chloride (10 eq, 42.5 mmol) is then added and the reaction mixture is stirred overnight at ambient temperature. The liquid is then removed and the resin is washed with dimethylformamide(3×), tetrahydrofuran(2×), dichloromethane(3×) and diethyl ether (1×) and dried overnight with a stream of nitrogen gas.

Step 8: Cleavage.

The resin is cleaved with 50% trifluoroacetic acid in dichloromethane for one hour to yield the title compound (82.5% pure by ELSD). Expected product MW is 563. Observed product MW is 563.

EXAMPLE 7

Preparation of Imidazo[1,5-a]pyrazine-7(1H)-carboxylic acid, 2(4-methoxyphenyl)hexahydro-1,3-dioxo-etyl ester

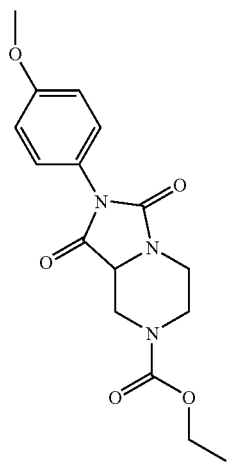

Step 1: Reductive Amination on the BAL Resin.

BAL resin is swelled in a 1% acetic acid in dimethylformamide solution. Beta-Alanine-tertbutyl ester hydrochloride (20.0 mmol) and sodium triacetoxyborohydride (20.0 mmol) are added sequentially. The reaction mixture is stirred at ambient temperature for 6.5 hours. The liquid is then removed and the resin is washed with 1:1 dimethylformamide/methanol (2×), dimethylformamide (2×), dichloromethane (3×) and diethyl ether (1×) and dried overnight with a stream of nitrogen gas.

Step 2: Acylation with 1-Alloc-4-Fmoc-piperazine-2-carboxylic Acid.

Dimethylformamide is added to swell the resin prepared in step 1 above. 1-Aloc-4-fmoc-piperazine-2-carboxylic acid (180.0 mmol) is dissolved in dimethylformamide and added to the resin. O-Benzotriazol-1-yl-N,N,N',N'-tetramethyluronium hexafluorophosphate (180.0 mmol) and diisopropylethylamine (360.0 mmol) are then added sequentially. The reaction mixture is stirred at ambient temperature for 6.5 hours. The liquid is removed and the resin is washed with dimethylformamide (3×), dichloromethane (3×) and diethyl ether (1×) and dried overnight with a stream of nitrogen gas.

Step 3: Fmoc Deprotection.

Dimethylformamide and piperidine are added to the above resin prepared in step 2 above and the reaction mixture is stirred at ambient temperature for 3.5 hours. The liquid is then removed and the resin is washed with dimethylformamide (3×), dichloromethane (3×), and diethyl ether (1×) and dried overnight with a stream of nitrogen gas.

Step 4: Carbamate Formation.

The resin prepared in step 3 above is swelled in anhydrous dichloromethane. DIEA (50.0 mmol) and ethyl chloroformate (50.0 mmol) are then added sequentially. The reaction mixture is stirred overnight at ambient temperature. The liquid is then removed and the resin is washed with dimethylformamide (2×), tetrahydrofuran (1×), dichloromethane (2×), and diethyl ether (1×) and dried overnight with a stream of nitrogen gas.

Step 5: Alloc Deprotection.

Tetrahydrofuran, dimethylsulfoxide and 0.5N hydrochloric acid (2:2:1) are added to the resin prepared in step 4 above. The reaction flask is flushed with nitrogen and $Pd(Ph_3P)_4$ (6.98 mmol) and morpholine (2500 mmol) are added sequentially. The reaction mixture is stirred overnight under a flow of nitrogen gas. The liquid is then removed and the resin is washed with tetrahydrofuran (2×), sodium diethyldithiocarbamate [0.02M in dimethylformamide] (2×), dimethylformamide (2×), 0.5% diisopropylethylamine in dichloromethane (1×), dichloromethane (3×) and diethyl ether (1×) and dried overnight with a stream of nitrogen gas.

Step 6: Urea Formation

The resin prepared in step 5 above is swelled in anhydrous dichloromethane. 4-Methoxyphenyl isocyanate (20.0 mmol) is added. The reaction mixture is stirred overnight at ambient temperature. The liquid is then removed and the resin is washed with dimethylformamide (2×), dichloromethane (3×), and diethyl ether (1×) and dried overnight with a stream of nitrogen gas.

Step 7: Cleavage.

The resin prepared in step 6 above is cleaved with 50% trifluoroacetic acid in dichloromethane for one hour and concentrated down to yield a 3 to 1 ratio of cyclized title compound to uncyclized precursor. This product is redissolved up into dichloromethane to give a dilute solution. A few drops of trifluoroacetic acid are added to catalyze the cyclization. The reaction is stirred at ambient temperature for 3 days. The title compound (89% pure by LC) is obtained upon concentration. Expected product MW is 333. Observed product MW is 333.

EXAMPLE 8

Preparation of a 10,000 Member piperazine-2-Carboxamide Library

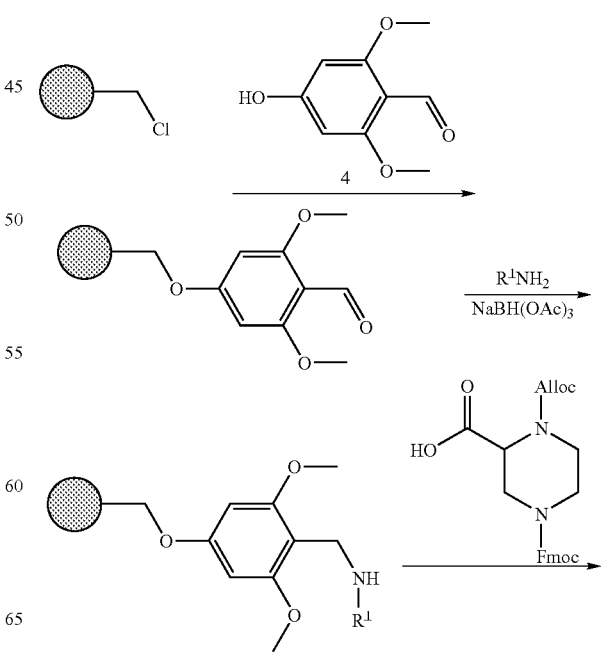

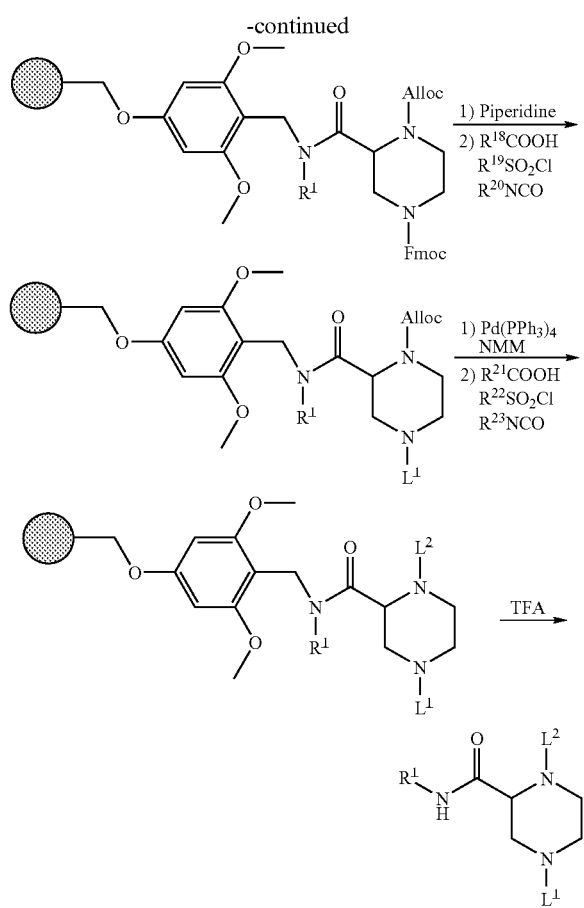

Ten thousand single compounds are prepared in two full matrix libraries of 5000 compounds each. Eighteen amines, Wang resin, and Rink amide resin are used at the $R^1$ postion of the scaffold. These same twenty inputs are used for both of the 5000 member libraries. For one library, twenty carboxylic acids, four chloroformates and a Boc group (to yield a free amine upon deprotection) are loaded onto the scaffold at the $R^2$ position. Five isocyanates, four sulfonyl chlorides and a free amine are used at the $R^3$ position. For the other library, five isocyanates and five sulfonyl chlorides are reacted at the $R^3$ position. Twenty carboxylic acids, four chloroformates and a free amine are used at the $R^3$ position.

Reductive Amination on the BAL Resin:

The library is constructed as two full matrix libraries of 5000 compounds each. For each half of the library:

For each amine, 250 MicroKans™ (each MicroKan™ contains 10 mg of 1.0 mmol/g loaded BAL resin) are placed into a 1.0 L 3-necked round bottom flask fitted with an overhead stirrer. The resin in the MicroKans™ is swelled in 1% acetic acid/dimethylformamide (300 ml). The air bubbles in the MicroKans™ are removed by placing the round bottom flask under vacuum. The amine (20.0 mmol) and sodium triacetoxyborohydride (4.24 g, 20.0 mmol) are added sequentially. The reaction is stirred at ambient temperature for 6.5 hours. Each is then individually drained and washed with dimethylformamide (1×). All of the Micro-Kans™ are then combined and washed with 1:1 dimethylformamide/methanol (2×), dimethylformamide (2×), dichloromethane (3×) and diethyl ether (1×). The kans are then dried overnight with a stream of nitrogen gas.

Acylation of Reductively Aminated BAL Resin with 1-Alloc-4-Fmoc-piperazine-2-Carboxylic Acid (9000 kans).

For each half of the library:

The 4500 MicroKans™ previously reacted with amines are placed into a 12 L 3-necked round bottom flask fitted with an overhead stirrer. Dimethylformamide (4.5 L) is added to swell the resin in the MicroKans. 1-Alloc-4-fmoc-piperazine-2-carboxylic acid (78.6 g, 180.0 mmol) is dissolved in dimethylformamide (500 ml) and added to the MicroKans. O-Benzotriazol-1-yl-N,N',N'-tetramethyluronium hexafluorophosphate (68.3 g, 180.0 mmol) and diisopropylethylamine (62.7 ml, 360.0 mmol) are then added sequentially. The reaction mixture is stirred at ambient temperature for 6.5 hours. The solution is drained off and the MicroKans are washed with dimethylformamide (3×), dichloromethane (3×) and diethyl ether (1×). The Micro-Kans are dried overnight with a stream of nitrogen gas.

Acylation of Wang resin with 1-Alloc-4-Fmoc-piperazine-2-Carboxylic Acid (500 kans).

Wang resin (5.0 g of 1.7 mmol/g loaded resin from Polymer Labs) is swelled in anhydrous dichloromethane (80 ml). 1-Alloc-4-fmoc-piperazine-2-carboxylic acid (7.42 g, 17.0 mmol), diisopropylcarbodiimide (2.67 ml, 17.0 mmol) and 4-dimethylaminopyridine (0.21 g, 1.70 mmol) are added sequentially. The reaction is then stirred overnight at ambient temperature on an orbital shaker. The reaction solution is drained off and the resin is washed with dichloromethane (2×), dimethylformamide (4×), dichloromethane (4×), tetrahydrofuran (4×) and diethyl ether (4×) and dried in vacuo. IR analysis is used to confirm the loading of the scaffold. This resin is then loaded into 500 MicroKans.

Acylation of Rink Amide Resin with 1-Alloc-4-Fmoc-piperazine-2-Carboxylic Acid (500 kans).

Fmoc-Rink Amide resin (11.0 g of 0.78 mmol/g loaded resin from Advanced Chemtech) is deprotected with 1:1 dimethylformamide/piperidine for 3 hours. The reaction solution is drained off and the resin is washed with dimethylformamide (4×), tetrahydrofuran (4×), diethyl ether (3×) and anhydrous dimethylformamide (3×). Anhydrous dimethylformamide (120 ml) is then added to the resin. 1-Alloc-4-fmoc-piperazine-2-carboxylic acid (14.98 g, 34.32 mmol), O-Benzotriazol-1-yl-N,N,N',N'-tetramethyluronium hexafluorophosphate (13.0 g, 34.32 mmol) and diisopropylethylamine (12.0 ml, 68.64 mmol) are added sequentially. The reaction mixture is stirred on an orbital shaker at ambient temperature overnight. The reaction solution is drained off and the resin is washed with dimethylformamide (4×), dichloromethane (4×), tetrahydrofuran (4×), and diethyl ether (4×) and dried in vacuo. IR analysis is used to confirm the loading of the scaffold. This resin is then loaded into 500 MicroKans.

Fmoc Deprotection.

For each half of the library:

The 5000 MicroKans are placed into a 12 L 3-necked round bottom flask fitted with an overhead stirrer. Dimethylformamide (2.5 L) and piperidine (2.5 L) are added to the MicroKans. The reaction is stirred at ambient temperature for 3.5 hours. The reaction solution is then drained off and the MicroKans are washed with dimethylformamide (3×), dichloromethane (3×), and diethyl ether (1×). The Micro-Kans are then dried overnight with a stream of nitrogen gas.

Acylation with Carboxylic Acids.

For each carboxylic acid, 200 MicroKans are placed in a one liter 3-necked round bottom flask fitted with an overhead stirrer. The resin in the kans is swelled in 1-methyl-2- pyrrolidinone (300 ml). The carboxylic acid (20.0 mmol) and 1-[3-(dimethylamino)propyl]-3-ethylcarbodiimide hydrochloride (3.83 g, 20.0 mmol) are added sequentially and the reaction is stirred overnight at ambient temperature. Each MicroKan™ is then individually drained and washed once with dimethylformamide. All of the MicroKans from each acid are then combined and washed with dimethylformamide (2×), dichloromethane (3×), and diethyl ether (1×). The MicroKans™ are then dried overnight with a stream of nitrogen gas.

Acylation with Chloroformates:

For each chloroformate, 200 MicroKans™ are placed into a one liter 3-necked round bottom flask fitted with an overhead stirrer. The resin in the MicroKans™ is swelled in anhydrous dichloromethane (300 ml). diisopropylethylamine (3.5 ml, 20.0 mmol) and the chloroformate (20.0 mmol) are then added sequentially. The reaction is stirred overnight at ambient temperature. Each MicroKan™ is then individually drained and washed once with dimethylformamide. All of the MicroKans™ from each chloroformate are then combined and washed with dimethylformamide (2×), dichloromethane (3×) and diethyl ether (1×). The MicroKans™ are then dried overnight with a stream of nitrogen gas.

Urea Formation with Isocyanates:

For each isocyanate, 500 MicroKans™ are placed into either a two or three liter 3-necked round bottom flask fitted with an overhead stirrer. The resin in the MicroKans™ is swelled in anhydrous dichloromethane (600 ml). The isocyanate (50.0 mmol) is then added neat. The reaction is stirred overnight at ambient temperature. Each MicroKan™ is then individually drained and washed with dimethylformamide (3×). All of the MicroKan™ from each isocyanate are then combined and washed with dimethylformamide (2×), tetrahydrofuran (1×), dichloromethane (2×), and diethyl ether (1×). The MicroKans™ are then dried overnight with a stream of nitrogen gas.

Sulfonamide Formation:

For each sulfonyl chloride, 500 MicroKans™ are placed into either a two or three liter 3-necked round bottom flask fitted with an overhead stirrer. The resin in the MicroKans™ is swelled in anhydrous dichloromethane (600 ml). N-methylmorpholine (5.5 ml, 50.0 mmol) and the sulfonyl chloride (50.0 mmol) are then added sequentially. The reaction is stirred overnight at ambient temperature. Each MicroKan™ is then individually drained and washed with dimethylformamide (3×). All of the MicroKans™ from each sulfonyl chloride are then combined and washed with dimethylformamide (2×), tetrahydrofuran (1×), dichloromethane (2×), and diethyl ether (1×). The MicroKans™ are then dried overnight with a stream of nitrogen gas.

Alloc Deprotection:

For each half of the library:

The 5000 MicroKans™ are placed into a 12 L 3-necked round bottom flask fitted with an overhead stirrer. Tetrahydrofuran (2L), dimethylsulfoxide (2L), and 0.5N hydrochloric acid (1L) are added to the MicroKans™. The reaction flask is then flushed with nitrogen. Pd(Ph$_3$P)$_4$ (8.06 g, 6.98 mmol) and morpholine (218 ml, 2500 mmol) are added sequentially. The reaction is stirred overnight under a flow of nitrogen gas. The reaction flask is drained and the MicroKans™ are washed with tetrahydrofuran (2×), sodium diethyldithiocarbamate (0.02M in dimethylformamide) (2×), dimethylformamide (2×), 0.5% diisopropylethylamine in dichloromethane (1×), dichloromethane (3×), and diethyl ether (1×). The MicroKans™ are then dried overnight with a stream of nitrogen gas.

Cleavage:

The three different resins used in this library are separated. The 9000 MicroKans™ containing BAL resin are clipped with 50% trifluoroacetic acid in dichloromethane for one hour. The 500 MicroKans™ containing Wang resin are clipped with 30% trifluoroacetic acid in dichloromethane for one hour. The 500 MicroKans™ containing Rink amide resin are clipped with 10% trifluoroacetic acid in dichloromethane for one hour. All of the above cleavage solutions contained a small amount of water. 99+% spectrophotometric grade trifluoroacetic acid is used. The cleavage plates are then concentrated down in a Savant from 25 to 43 degrees centigrade.

Representative reagents suitable for use in the foregoing library synthesis are listed in Tables 1, 2 and 3.

TABLE 1

| Entry | Resin | $R^1NH_2$ |
|---|---|---|
| 1 | BAL | 3-(2-oxopyrrolidin-1-yl)propylamine |
| 2 | BAL | 1-naphthalenylmethylamine |
| 3 | BAL | (tetrahydrofuran-2-yl)methylamine |
| 4 | BAL | benzylamine |
| 5 | BAL | 3,4-dimethoxybenzylamine |
| 6 | BAL | 3-(trifluoromethyl)benzylamine |
| 7 | BAL | 2-phenylethylamine |
| 8 | BAL | 3-(isopropoxy)propylamine |

TABLE 1-continued
| Entry | Resin | R¹NH₂ |
|---|---|---|
| 9 | BAL | 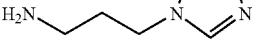 |
| 10 | BAL | 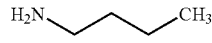 |
| 11 | BAL | 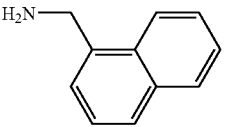 |
| 12 | BAL | ClH 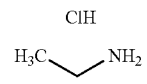 |
| 13 | BAL | ClH 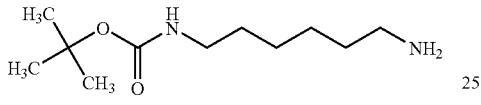 |
| 14 | BAL | 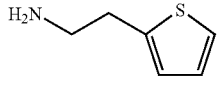 |
| 15 | BAL | ClH 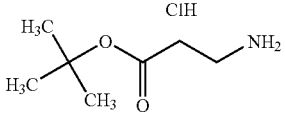 |
| 16 | BAL | 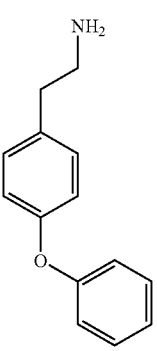 |
| 17 | BAL | ClH 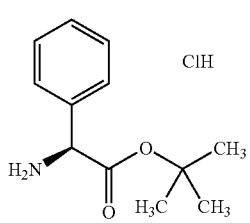 |
| 18 | BAL | 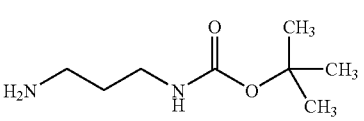 |
| 19 | RINK-Amide | |
| 20 | Wang | |
TABLE 2
| Entry | R¹⁸CO₂H; R¹⁹SO₂Cl; R²⁰NCO |
|---|---|
| 1 | BOC |
| 2 | 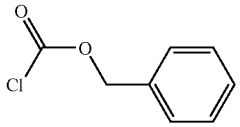 |
| 3 | 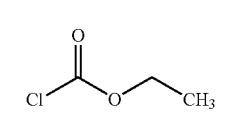 |
| 4 | 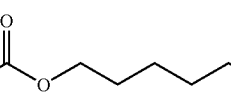 |
| 5 | 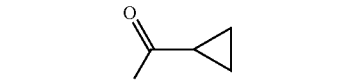 |
| 6 |  |
| 7 | 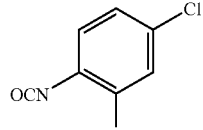 |
| 8 | 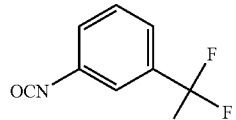 |
| 9 | 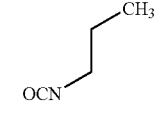 |
| 10 | 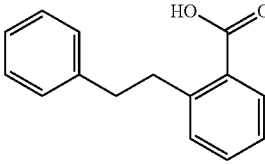 |
| 11 | 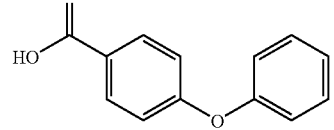 |

TABLE 2-continued

| Entry | $R^{18}CO_2H$; $R^{19}SO_2Cl$; $R^{20}NCO$ |
|---|---|
| 12 | 3,3-dimethylbutanoic acid |
| 13 | 3,3-diphenylpropanoic acid |
| 14 | 3-(3,4-dimethoxyphenyl)propanoic acid |
| 15 | 1-methyl-1H-pyrrole-2-carboxylic acid |
| 16 | furan-2-carboxylic acid |
| 17 | (E)-3-(1H-imidazol-4-yl)acrylic acid |
| 18 | 1H-indole-2-carboxylic acid |
| 19 | 3-(piperidin-1-yl)propanoic acid |
| 20 | quinoline-8-sulfonyl chloride |
| 21 | 4-tert-butylbenzenesulfonyl chloride |
| 22 | 1H-benzo[d][1,2,3]triazole-5-carboxylic acid |
| 23 | 3-(1H-indol-1-yl)propanoic acid |
| 24 | 2,5-dimethoxybenzenesulfonyl chloride |
| 25 | acetic acid |
| 26 | (2-isocyanatoethyl)benzene |
| 27 | 3-(tert-butoxycarbonylamino)propanoic acid |
| 28 | (S)-2-(tert-butoxycarbonylamino)-5-tert-butoxy-5-oxopentanoic acid |
| 29 | 2-(1H-tetrazol-1-yl)acetic acid |
| 30 | benzo[b]thiophene-2-carboxylic acid |
| 31 | 5-methyl-2-phenyl-2H-1,2,3-triazole-4-carboxylic acid |
| 32 | 2,6-dichloro-4-isocyanatopyridine |

TABLE 2-continued
| Entry | R$^{18}$CO$_2$H; R$^{19}$SO$_2$Cl; R$^{20}$NCO |
|---|---|
| 33 | 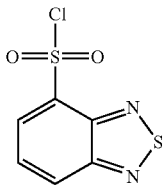 |
| 34 | 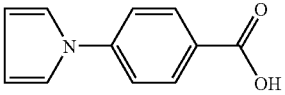 |
| 35 | 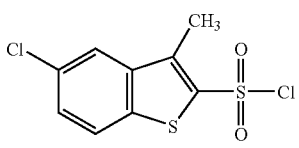 |
TABLE 3
| Entry | R$^{21}$CO$_2$H; R$^{22}$SO$_2$Cl; R$^{23}$NCO |
|---|---|
| 1 | H |
| 2 | 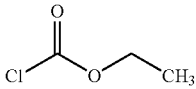 |
| 3 | 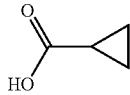 |
| 4 | 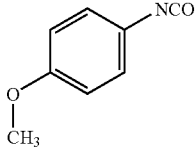 |
| 5 | 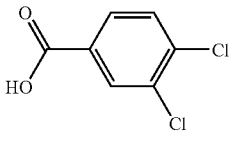 |
| 6 | 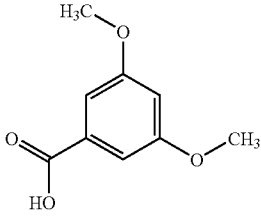 |
TABLE 3-continued
| Entry | R$^{21}$CO$_2$H; R$^{22}$SO$_2$Cl; R$^{23}$NCO |
|---|---|
| 7 | 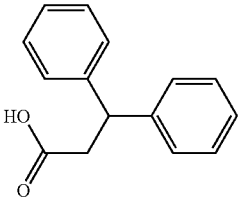 |
| 8 | 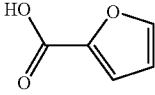 |
| 9 | 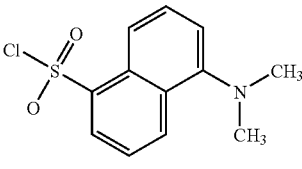 |
| 10 | 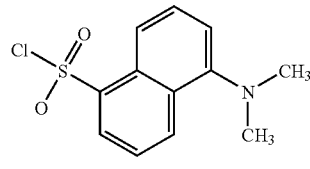 |
| 11 | 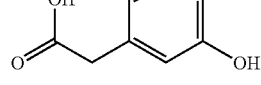 |
| 12 | 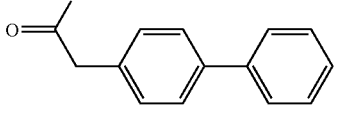 |
| 13 | 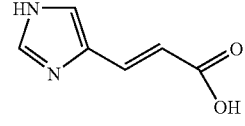 |
| 14 | 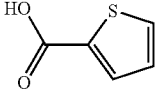 |
| 15 | 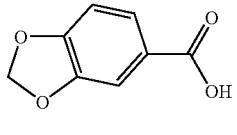 |
| 16 | 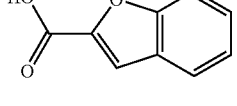 |
| 17 | 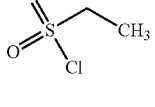 |

TABLE 3-continued

| Entry | $R^{21}CO_2H$; $R^{22}SO_2Cl$; $R^{23}NCO$ |
|---|---|
| 18 | 4-methoxyphenyl chloroformate |
| 19 | 1,3-benzodioxol-5-yl acetic acid |
| 20 | 3,5-bis(trifluoromethyl)benzenesulfonyl chloride |
| 21 | acetic acid |
| 22 | phenethyl isocyanate |
| 23 | N-Boc-β-alanine |
| 24 | 4-tert-butylcyclohexanecarboxylic acid |
| 25 | N-Boc-L-arginine (Chiral) |

TABLE 3-continued

| Entry | $R^{21}CO_2H$; $R^{22}SO_2Cl$; $R^{23}NCO$ |
|---|---|
| 26 | quinoline-6-carboxylic acid |
| 27 | 5-chlorothiophene-2-sulfonyl chloride |
| 28 | 2-(thiophen-2-yl)ethyl isocyanate |
| 29 | 2-naphthyl chloroformate |
| 30 | N-Boc-L-histidine |
| 31 | 2,3-dihydro-1H-indene-2-acetic acid |
| 32 | neopentyl chloroformate |
| 33 | 2-phenoxyphenyl isocyanate |
| 34 | 4-(dimethylamino)phenyl isocyanate |

EXAMPLE 9

Preparation of a 5,000 Member Piperazine-2-Carboxamide Library

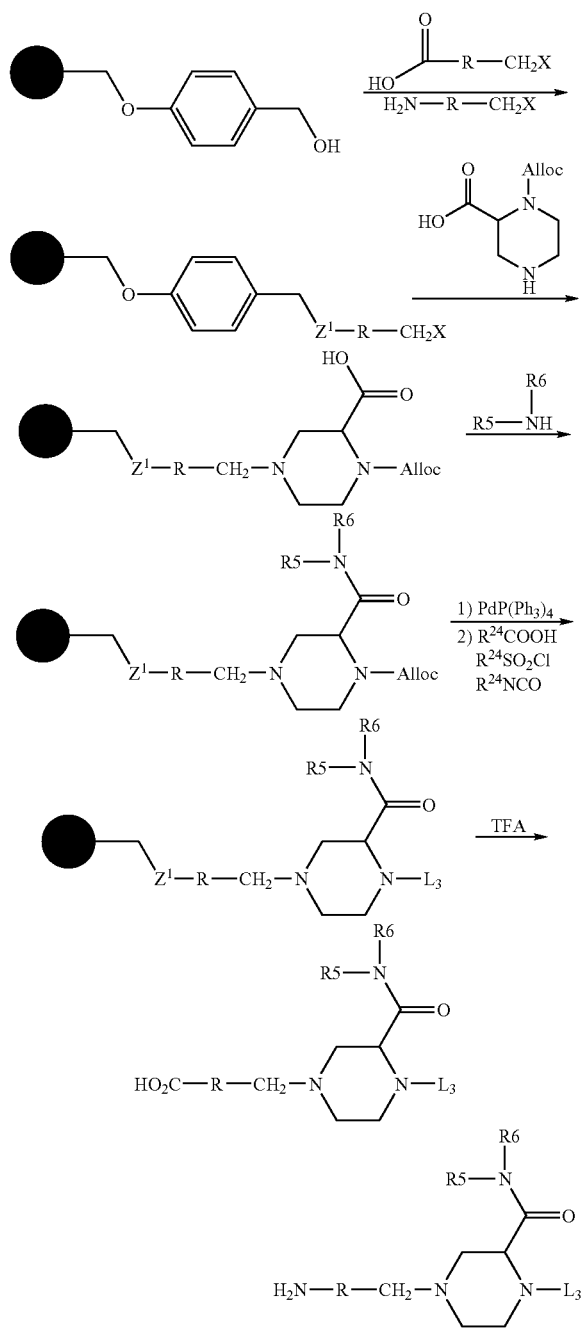

Bi-functional pieces containing a handle (carboxylic acid, amine) and a halide are loaded on Wang resin and then alkylated with 6. Bromo—or—Chloro carboxylic acids are loaded on Wang resin using either the Yamaguchi Method (2,6 dichlorobenzoyl chloride) or by conversion to the acid chloride. Alternatively Fmoc-amino acids are loaded on Wang resin with diisopropylcarbodiimide-4-dimethylaminopyridine, the Fmoc group is removed and the free amine is acylated with bromo or chloro carboxylic acids. Symmetrical diamines are also loaded on the nitrophenol carbonate derivative of Wang and acylated with bromo or chloro carboxylic acids. The carboxylic acid is then reacted with amines in a second combinatorial step and after removal of the alloc group the third combinatorial step consists of acylation, sulfonylation or urea formation.

Loading of Bromo-acids: Yamaguchi Method.

4-(Bromomethyl)phenylacetic acid (529 mg, 2.34 mmol) is poured into 5 ml of dimethylformamide. Pyridine (170 ul, 2.125 mmol) and 2,6-dichlorobenzoylchloride (301ul, 2.125 mmol) are then added. The mixture is shaken for 1 hour and then Wang resin (loading 1.7 mmol/g) is added to the mixture. The reaction mixture is shaken overnight. The reaction mixture is then drained and the resin is washed with dimethylformamide (3×), tetrahydrofuran (3×), dichloromethane (3×), and diethyl ether (2×) and dried in vacuo.

Loading of Acid Chlorides.

In a flask flushed with nitrogen, the acid (5.5 eq, 2.34 mmol), and oxalyl chloride (3 ml, 6.02 mmol) are mixed in dichloromethane (10 ml). One drop of dimethylformamide is added. The mixture is stirred for one hour. The solvent and the oxalyl chloride are removed by evaporation. The acid chloride is dried overnight in vacuo.

The acid choride is dissolved in 9 ml of dichloromethane/pyridine (9:1). Wang resin (loading 1.7 mmol/g) is added and the mixture is shaken overnight. The mixture is drained and the resin is washed with dimethylformamide (3×), tetrahydrofuran (3×), dichloromethane(3×), and diethyl ether (2×) and dried in vacuo.

Loading of Fmoc-Amino Acids and Coupling to bromo acids: diisopropylcarbodiimide/4-dimethylaminopyridine.

Wang resin (150 mg, 0.255 mmol) is suspended in dichloromethane (2 ml). The acid (5 eq, 1.25 mmol) is added, followed by diisopropylcarbodiimide (200 ul, 1.25 mmol) and 4-dimethylaminopyridine (6.4 mg, 0.052 mmol). The mixture is shaken overnight. The mixture is drained and the resin is washed with dichloromethane (2×), dimethylformamide (3×), tetrahydrofuran (3×), dichloromethane (3×) and ether (2×) and dried in vacuo.

Removal of Fmoc Group:

The resin (150 mg, 0.255 mmol) is suspended in piperidine/dimethylformamide (1:1) and the mixture is shaken overnight. The mixture is drained and the resin is washed with dichloromethane (2×), dimethylformamide (3×), tetrahydrofuran (3×), dichloromethane (3×) and diethyl ether (2×) and dried in vacuo.

Loading of Symmetrical Diamines:

Nitrophenol carbonic resin (50 mg, 0.08 mmol) is suspended in 1 ml of dimethylformamide. The diamine (0.8 mmol) is added and the mixture is shaken overnight at ambient temperature. The mixture is drained and the resin is washed with dimethylformamide(3×), tetrahydrofuran(3×), dichloromethane(3×) and diethyl ether (2×).

Coupling

The resin (100 mg, 0.17 mmol) is suspended in dichloromethane (10 ml). The bromoacid (1.7 mmol) and diisopropylcarbodiimide (267 ul, 1.7 mmol) are added and the mixture is shaken overnight. The mixture is drained and the resin is washed with dichloromethane (2×), dimethylformamide (3×), tetrahydrofuran (3×), dichloromethane (3×), and ether (2×) and dried in vacuo.

Alkylation with piperazine-2-carboxamide Scaffold:

The resin prepared as described above (4.6 g, 7.82 mmol) is suspended in dimethylformamide (15 ml). 1-Alloc-2-carboxy-piperidine.trifluoroacetic acid salt (2.71 g, 23.4 mmol), potassium iodide (458 mg, 23.4 mmol) and diisopropylethylamine (2.89 ml, 45 mmol) are added and the reaction mixture is heated overnight at 80° C. The reaction mixture is drained and the resin is washed with dimethylformamide (3×), tetrahydrofuran (3×), dichloromethane (3×), and diethyl ether (1×).

Amide Bond Formation:

The library is constructed as one full matrix library of 5100 compounds.

For each amine, 402 MicroKans™ (each MicroKan™ contains 6 mg of 1.7 mmol/g loaded resin) are placed into a 1.0 L 3-necked round bottom flask fitted with an overhead stirrer. The resin in the MicroKans™ is swelled in dimethylformamide solution (300 mL). Diisopropylcarbodiimide (4.79 ml) and pentafluorophenol (5.63 g) are added and the mixture is stirred at ambient temperature for two hours. Each reaction mixture is drained and the MicroKans™ are washed with dimethylformamide (2×). The MicroKans™ in each round bottom flask are again suspended in dimethylformamide(300 ml) and the corresponding amine (10 eq., 20.4 mmol) is added to each vessel. If the HCl salt of the amine is utilized, 10 eq. of diisopropylethylamine is added. The reaction mixture is allowed to stir at ambient temperature overnight. Each MicroKan™ is individually drained. All of the MicroKans™ are then combined and washed with dimethylformamide (3×), tetrahydrofuran (3×), dichloromethane (3×), and ether (1×). The kans are dried overnight with a stream of nitrogen.

Alloc Deprotection:

The 5100 MicroKans™ are placed into a 12 L 3-necked round bottom flask fitted with an overhead stirrer. Tetrahydrofuran (2L), dimethylsulfoxide (2L), and 0.5N hydrochloric acid (1L) are added to the reaction flask. The reaction flask is flushed with nitrogen and $Pd(Ph_3P)_4$ (8.06 g, 6.98 mmol) and morpholine (218 ml, 2500 mmol) are added sequentially. The reaction is stirred overnight under a flow of nitrogen gas. The reaction is drained and the MicroKans™ are washed with tetrahydrofuran (2×), sodium diethylditbiocarbamate (0.02M in dimethylformamide) (2×), dimethylformamide (2×), 0.5% diisopropylethylamine in dichloromethane (1×), dichloromethane (3×), and ether (1×). The MicroKans™ are then dried overnight with a stream of nitrogen gas.

Acylation with Carboxylic Acids:

For each carboxylic acid, 425 MicroKans™ are placed into either a two or three liter 3-necked round bottom flask fitted with an overhead stirrer. The resin in the MicroKans™ is swelled in dimethylformamide (300 ml). Diisopropylethylamine (40 eq, 14.81 ml) and O-benzotriazol-1-yl-N,N,N',N'-tetramethyluronium hexafluorophosphate (20 eq, 32.24 g) are added to the vessel. The carboxylic acid (20 eq, 85 mmol) is added. The reaction is stirred overnight at ambient temperature. Each MicroKan™ is individually drained and washed once with dimethylformamide. All of the MicroKans™ are then combined and washed with dimethylformamide (3×), tetrahydrofuran(2×), dichloromethane(3×), and diethyl ether (1×). The MicroKans™ are then dried overnight with a stream of nitrogen gas.

Acylation with Chloroformates:

For the one chloroformate, 425 MicroKans™ are placed into a two liter 3-necked round bottom flask fitted with an overhead stirrer. The resin in the MicroKans™ is swelled with dichloromethane/pyridine (1350 ml dichloromethane: 150 ml pyridine). The chloroformate (10 eq, 85 mmol) is added. The reaction is stirred overnight at ambient temperature. Each MicroKan™ is individually drained and washed once with dichloromethane. All of the MicroKans™ are then combined with the MicroKans™ reacted with the carboxylic acid and washed with dimethylformamide(3×), tetrahydrofuran(2×), dichloromethane(3×), and ether(1×). The MicroKans™ are then dried overnight with a stream of nitrogen gas.

Sulfonamide Formation:

For each sulfonyl chloride, 425 MicroKans™ are placed into either a two or three liter 3-necked round bottom flask fitted with an overhead stirrer. The resin in the kans is swelled with dichloromethane/pyridine (1350 ml dichloromethane:150 ml pyridine). The sulfonyl chloride (10 eq, 42.5 mmol) is then added. The reaction is stirred overnight at ambient temperature. Each MicroKan is individually drained and washed with dimethylformamide(3×), tetrahydrofuran(2×), dichloromethane(3×), and ether (1×). The MicroKans™ are dried overnight with a stream of nitrogen gas.

Cleavage:

The 5100 MicroKans™ containing the various 17 resins are clipped with 50% trifluoroacetic acid in dichloromethane for one hour. The cleavage solutions contained a small amount of water (300 ml of trifluoroacetic acid, 300 ml of dichloromethane, 10 ml of water). 99+% spectrophotometric grade trifluoroacetic acid is used. The cleavage plates are then concentrated down in a Savant from 25 to 43 degrees centigrade.

Representative reagents suitable for use in the foregoing library synthesis are listed in Tables 4, 5 and 6.

TABLE 4

| Entry | Resin | $HO_2C-R^7-CH_2-X$ $H_2N-R^7-CH_2-X$ | Loading Method |
|---|---|---|---|
| 1 | Wang-nitrophenyl carbonate | [structure: cyclohexane with H₂N and HN-C(=O)-CH₂-Br substituents] | Loading of diamine, acylation with bromoacetic acid |

TABLE 4-continued

| Entry | Resin | HO₂C—R⁷—CH₂—X / H₂N—R⁷—CH₂—X | Loading Method |
|---|---|---|---|
| 2 | Wang | bromoacetic acid | Yamaguchi |
| 3 | Wang-nitrophenyl carbonate | 1-(bromoacetyl)piperazine | Loading of diamine, acylation with bromoacetic acid |
| 4 | Wang | N-[2-(4-bromomethylphenyl)acetyl]-β-alanine | Loading of Fmoc-beta alanine, deprotection, acylation with p-bromophenyl phenyl acetic acid. |
| 5 | Wang-nitrophenyl carbonate | N-(3-aminopropyl)-2-bromoacetamide | Loading of diamine, acylation with bromoacetic acid |
| 6 | Wang-nitrophenyl carbonate | N-(3-aminopropyl)-2-[4-(bromomethyl)phenyl]acetamide | Loading of diamine, acylation with p-bromophenyl phenyl acetic acid. |
| 7 | Wang-nitrophenyl carbonate | N-[4-(aminomethyl)benzyl]-2-bromoacetamide | Loading of diamine, acylation with bromoacetic acid |
| 8 | Wang-nitrophenyl carbonate | N-[4-(aminomethyl)benzyl]-2-[4-(bromomethyl)phenyl]acetamide | Loading of diamine, acylation with p-bromophenyl phenyl acetic acid. |
| 9 | Wang | 2-[4-(bromomethyl)phenyl]acetic acid | Yamaguchi |

TABLE 4-continued

| Entry | Resin | $HO_2C-R^7-CH_2-X$ / $H_2N-R^7-CH_2-X$ | Loading Method |
|---|---|---|---|
| 10 | Wang-nitrophenyl carbonate | [structure: 4-aminocyclohexyl-NH-C(O)-CH2-Br] | Loading of diamine, acylation with bromoacetic acid |
| 11 | Wang-nitrophenyl carbonate | [structure: 4-aminocyclohexyl-NH-C(O)-CH2-(p-bromomethylphenyl)] | Loading of diamine, acylation with p-bromomethyl phenyl acetic acid. |
| 12 | Wang | [structure: HO2C-CH2CH2-NH-C(O)-CH2-Cl] | Fmoc-beta alanine, deprotection, coupling with chloro-acetic acid. |
| 13 | Wang | [structure: N-chloroacetyl proline] | Loading of Fmoc-proline, deprotection and acylation with chloroacetic acid. |
| 14 | Wang | [structure: 3-(chloromethyl)benzoic acid] | Acid Chloride |
| 15 | Wang | [structure: 4-(chloroacetylamino)benzoic acid] | Loading of Fmoc p-aminobenzoic acid, deprotection, acylation with chloroacetic acid |
| 16 | Wang | [structure: 2-(chloroacetylamino)thiazol-4-yl acetic acid] | Yamaguchi |
| 17 | Wang nitrophenyl carbonate | H | Direct reaction of the scaffold with nitro-phenyl carbonate Wang. |

TABLE 5

| Entry | HNR⁵R⁶ |
|---|---|
| 1 | H₂N-propyl-pyrrolidinone |
| 2 | 1-(aminomethyl)naphthalene |
| 3 | pyrrolidine |
| 4 | (tetrahydrofuran-2-yl)methanamine |
| 5 | 1-benzylpiperazine |
| 6 | piperidine |
| 7 | 4-phenylpiperidine |
| 8 | 3-(aminomethyl)pyridine |
| 9 | 2-(piperidin-1-yl)ethanamine |
| 10 | 1,2,3,4-tetrahydroisoquinoline |
| 11 | 2-phenylethanamine |
| 12 | 3,3-diphenylpropan-1-amine |
| 13 | 3-isopropoxypropan-1-amine |

TABLE 5-continued

| Entry | HNR⁵R⁶ |
|---|---|
| 14 | 3-(1H-imidazol-1-yl)propan-1-amine |
| 15 | 4-(2-aminoethyl)benzenesulfonamide |
| 16 | (S)-2-(methoxymethyl)pyrrolidine (Chiral) |
| 17 | butan-1-amine |
| 18 | (S)-tert-butyl 2-amino-3-(tert-butoxy)propanoate |
| 19 | cyclopropylmethanamine |
| 20 | 2-(thiophen-2-yl)ethanamine |
| 21 | N-(pyrrolidin-3-yl)acetamide |
| 22 | 2-(4-phenoxyphenyl)ethanamine |
| 23 | N,N-dimethylpyrrolidin-3-amine |

What is claimed is:

1. A method of preparing a substituted hydantoin of formula

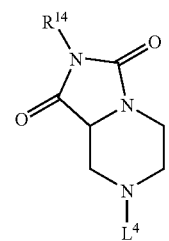

wherein
  $L^4$ is $Y^4R^{15}$;
  $Y^4$ is —C(O)—, —C(O)O—, —C(O)NR^{16}— or —SO_2—;
  $R^{14}$ is aromatic;
  $R^{15}$ is aliphatic or aromatic; and
  $R^{16}$ is H, aliphatic or aromatic;
comprising reacting acid with a resin-bound diazacycloalkyl-2-carboxy derivative of formula

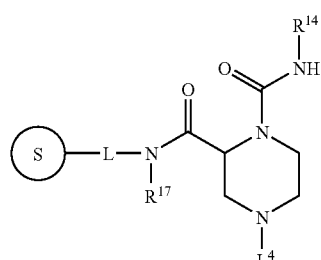

wherein

is a solid support;
  L is absent or a linking group; and
  $R^{17}$ is H, aliphatic or aromatic.

* * * * *